(12) United States Patent
Cotter

(10) Patent No.: US 8,716,302 B2
(45) Date of Patent: May 6, 2014

(54) COMPOUNDS FOR INDUCING CELLULAR APOPTOSIS

(75) Inventor: Finbarr Edward Cotter, London (GB)

(73) Assignee: Queen Mary & Westfield College, London (GB)

( * ) Notice: Subject to any disclaimer, the term of this patent is extended or adjusted under 35 U.S.C. 154(b) by 74 days.

(21) Appl. No.: 13/266,553

(22) PCT Filed: Apr. 28, 2010

(86) PCT No.: PCT/GB2010/000847
§ 371 (c)(1),
(2), (4) Date: Jan. 9, 2012

(87) PCT Pub. No.: WO2010/125343
PCT Pub. Date: Nov. 4, 2010

(65) Prior Publication Data
US 2012/0101115 A1  Apr. 26, 2012

(30) Foreign Application Priority Data

Apr. 28, 2009 (GB) .................................. 0907284.4

(51) Int. Cl.
| | | |
|---|---|---|
| *A01N 43/90* | (2006.01) |
| *A61K 31/519* | (2006.01) |
| *A01N 43/42* | (2006.01) |
| *A61K 31/44* | (2006.01) |
| *C07D 487/00* | (2006.01) |
| *C07D 217/00* | (2006.01) |
| *C07D 217/22* | (2006.01) |

(52) U.S. Cl.
USPC ....... 514/264.11; 514/310; 544/279; 546/143

(58) Field of Classification Search
None
See application file for complete search history.

(56) References Cited

U.S. PATENT DOCUMENTS

| | | | |
|---|---|---|---|
| 4,499,094 A | 2/1985 | Dubroeueq et al. | |
| 4,898,861 A | 2/1990 | Morgan et al. | |
| 4,966,906 A | 10/1990 | Glamkowski et al. | |
| 5,137,890 A * | 8/1992 | Sanfilippo et al. ......... | 514/264.1 |
| 5,998,624 A | 12/1999 | Goodman et al. | |
| 6,319,931 B1 | 11/2001 | Kroemer et al. | |
| 2009/0069300 A1 | 3/2009 | Zhou et al. | |

FOREIGN PATENT DOCUMENTS

| | | |
|---|---|---|
| FR | 2778564 A1 | 11/1999 |
| FR | 2894478 A1 | 6/2007 |
| JP | 7-165721 A | 6/1995 |
| WO | 01/44246 A1 | 6/2001 |
| WO | 03/059352 A2 | 7/2003 |
| WO | 2006/018625 A2 | 2/2006 |
| WO | 2008/096218 A1 | 8/2008 |
| WO | 2009/000087 A1 | 12/2008 |

OTHER PUBLICATIONS

Castedo, M., et al., Mitochondrial apoptosis and the peripheral benzodiazepine receptor: a novel target for viral and pharmacological manipulation, J Exp Med. Nov. 4, 2002;196(9):1121-5.
Gonzalez-Polo, R. A., et al., PK11195 potently sensitizes to apoptosis induction independently from the peripheral benzodiazepin receptor, Oncogene. Nov. 17, 2005;24(51):7503-13.

* cited by examiner

*Primary Examiner* — Jeffrey H Murray
(74) *Attorney, Agent, or Firm* — Pepper Hamilton, LLP

(57) ABSTRACT

The present invention provides isoquinoline, tetrahydroisoquinoline and tetrahydropyridopyrimidine compounds that induce cell death by apoptosis and uses of the compounds in medicine, especially their use for treating cancer and other diseases.

21 Claims, 3 Drawing Sheets

COMPOUNDS FOR INDUCING CELLULAR APOPTOSIS

Cross-Reference To Related Applications

This application is the U.S. National Stage filing of International Application Serial No. PCT/GB2010/000847 filed Apr. 28, 2010, which claims priority to Great Britain Application No. 0907284.4 filed Apr. 28, 2009, each of which is incorporated herein by reference in its entirety.

FIELD OF THE INVENTION

This invention relates to compounds that induce cell death by apoptosis by causing generation of reactive oxygen species (ROS) within mitochondria such as through Complex I of the mitochondrial electron transport chain or NADPH oxidase and their use for treating cancer and other diseases.

BACKGROUND OF THE INVENTION

Many cancer therapeutics rely on initiation of apoptosis. Problems seen with cancer therapeutics include drug resistance and toxicity (arising from insufficient selectivity). The selective induction of apoptosis in tumour cells versus normal cells is a key goal of cancer therapeutic drug discovery. One drug designed to selectively induce apoptosis is the isoquinoline carboxamide PK11195 (1-(2-chlorophenyl)-N-methyl-N-(1-methylpropyl)-3-isoquinolinecarboxamide). PK11195 does, however, have limitations in a clinical setting, for example in terms of poor solubility and dosage levels required.

Previously, PK11195 was thought to induce apoptosis by interaction with the peripheral benzodiazepine receptor (PBR). The PBR has been implicated in the regulation of the permeability transition pore complex (PTPC), opening of which results in mitochondrial membrane depolarisation, causing the release of cytochrome c and initiating a series of steps that leads to cell death by apoptosis.

More recently, it has been reported that functions have been erroneously ascribed to the PBR in the cellular effects of PK11195. Instead, it has been determined that PK11195 acts by a PBR independent intracellular mechanism involving intra-mitochondrial superoxide (WO 2006/018625, the contents of which are incorporated herein by reference). The mechanism of action ascribed to PK11195 in WO 2006/018625, involves the internalisation of PK11195 within mitochondria, enzymatic action of NADPH oxidase on PK11195 to remove a chlorine atom from PK11195 and replacement of the removed chlorine atom with an oxygen atom, thereby turning PK11195 into a reactive oxygen species (ROS) by superoxidation. The reactive oxygen species affects the redox sensitive mitochondrial membrane permeability transition pore complex (PTPC), resulting in mitochondrial membrane depolarisation, which causes the release of cytochrome c and initiates a series of steps leading to cell death by apoptosis.

Determination of this mechanism of action provides an important route for selectively inducing apoptosis of tumour cells, useful for example in treating cancer, in particular NADPH oxidase-positive cancers. The object of the invention is therefore to provide compounds which are capable of inducing apoptosis by the mechanism of action described above, with improved potency, efficacy and drugability. It has now been determined that certain classes of compounds show good efficacy in inducing cell apoptosis by the intra-mitochondrial superoxidation mechanism described above.

SUMMARY OF THE INVENTION

Accordingly, in a first aspect the present invention provides a compound of Formula (A) or a pharmaceutically acceptable salt thereof

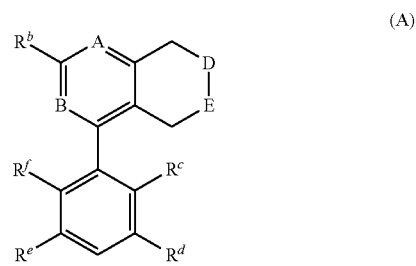

wherein A and B are both N, D is $CH_2$ and E is N—$R^a$ or wherein A and B are both CH, D is N—$R^a$ and E is $CH_2$;

$R^c$, $R^d$, $R^e$ and $R^f$ are each independently hydrogen, lower alkyl, —$NH_2$, —$NO_2$, —OH, —CN or halogen, provided that at least one of $R^c$ and $R^f$ is halogen;

$R^a$ is —$R^g$ or —C(O)$R^g$, wherein $R^g$ is optionally substituted aliphatic, haloalkyl, aryl, heteroaryl, alkylaryl, alkylheteroaryl, carbocycle or heterocycle; and $R^b$ is hydrogen, —$NO_2$, —$NH_2$, —NHC(O)$R^h$, —C(O)NH$R^h$ or —NHS(O)$_2R^h$, wherein $R^h$ is optionally substituted aliphatic, alkylaryl, alkylheteroaryl, aryl, heteroaryl, carbocycle or heterocycle. In certain embodiments, $R^b$ is not hydrogen.

Compounds of formula (A) may be tetrahydropyridopyrimidine compounds of formula (I) or tetrahydroisoquinoline compounds of formula (II), wherein such compounds are as defined below.

The first aspect of the present invention therefore provides a compound of Formula (I), or a pharmaceutically acceptable salt thereof,

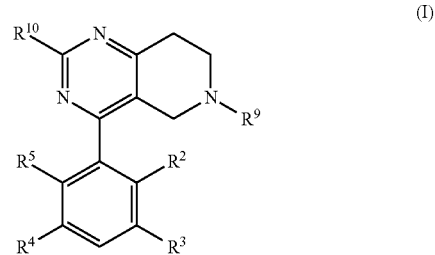

wherein $R^2$, $R^3$, $R^4$ and $R^5$ are each independently hydrogen, lower alkyl, —$NH_2$, —$NO_2$, —OH, —CN or halogen, provided that at least one of $R^2$ and $R^5$ is halogen;

$R^9$ is —$R^{11}$ or —C(O)$R^{11}$, wherein $R^{11}$ is optionally substituted aliphatic, haloalkyl, aryl, heteroaryl, alkylaryl, alkylheteroaryl, carbocycle or heterocycle; and $R^{10}$ is —$NO_2$, —$NH_2$, —NHC(O)$R^{12}$, —C(O)NH$R^{12}$ or —NHS(O)$_2R^{12}$, wherein $R^{12}$ is optionally substituted aliphatic (e.g. alkyl), alkylaryl, alkylheteroaryl, aryl, heteroaryl, carbocycle or heterocycle (such as aryl or cycloalkyl). $R^{12}$ is preferably optionally substituted alkyl, cycloalkyl or aryl.

In certain embodiments, $R^2$, $R^3$, $R^4$ and $R^5$ are each independently hydrogen or halogen, provided that at least one of $R^2$ and $R^5$ is halogen.

In certain embodiments, $R^3$ and $R^4$ are hydrogen.

In certain embodiments, one of $R^2$ and $R^5$ is halogen, preferably chlorine. Preferably, the other of $R^2$ and $R^5$ is hydrogen. In alternative embodiments, both of $R^2$ and $R^5$ are halogen, preferably chlorine.

In some embodiments, where $R^9$ is —$R^{11}$, $R^{11}$ is optionally substituted alkylaryl or alkylheteroaryl, for example optionally substituted benzyl.

In some embodiments, $R^9$ is benzyl. Alternatively, $R^9$ may be —C(O)$R^{11}$, wherein $R^{11}$ is alkyl or haloalkyl (for example $CF_3$ or $CH_2CH_2CH_3$) or substituted or unsubstituted aryl. Where $R^9$ is —C(O)$R^{11}$, $R^{11}$ is preferably haloalkyl or optionally substituted aryl.

In some embodiments, $R^{10}$ is —NHC(O)$R^{12}$. Preferably, $R^{12}$ is $C_{4-12}$ alkyl, preferably $C_{4-6}$ alkyl, preferably butyl, more preferably n-butyl.

The values described above for $R^2$, $R^3$, $R^4$, $R^5$, $R^9$, $R^{10}$, $R^{11}$ and $R^{12}$ may be present in any combination thereof in compounds of formula (I).

In certain particular embodiments, the compound of formula (I) is selected from:

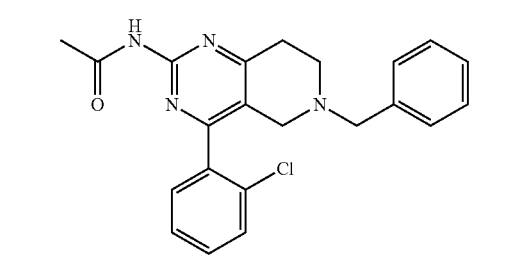

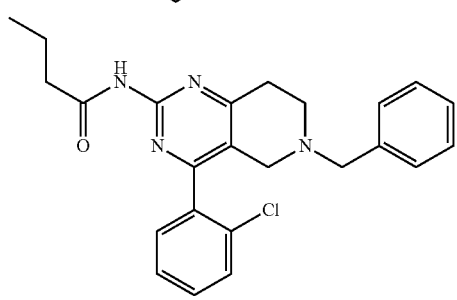

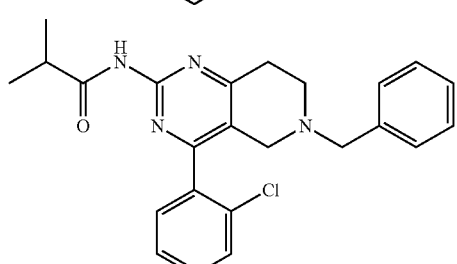

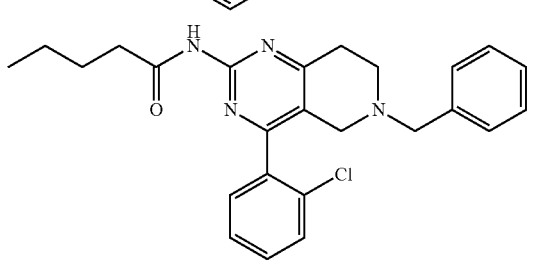

-continued

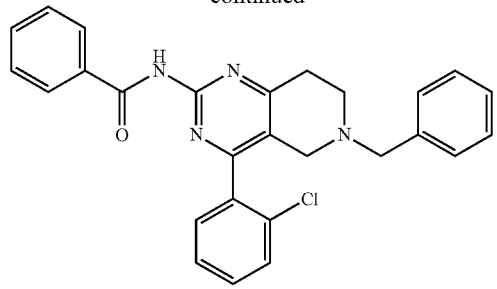

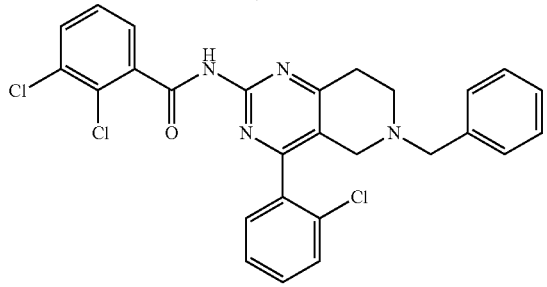

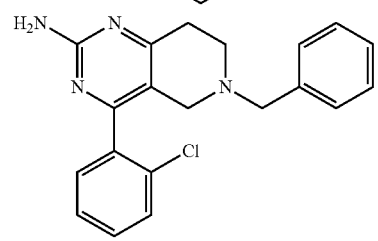

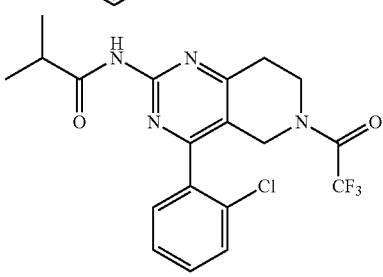

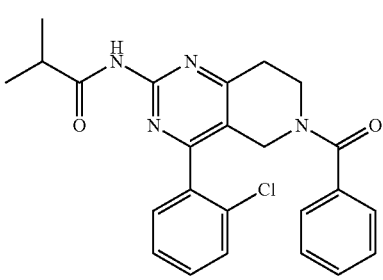

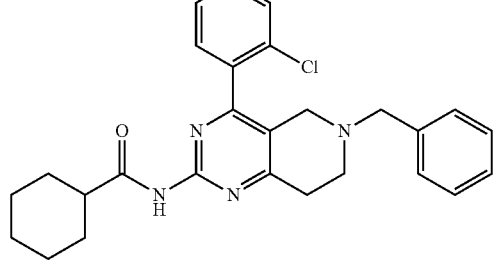

-continued

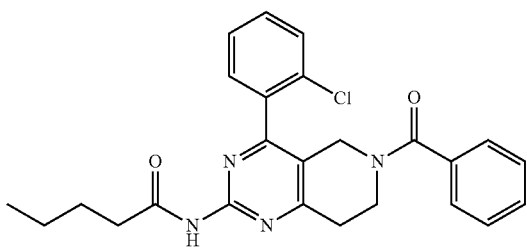

The first aspect of the invention also provides a compound of Formula (II) or a pharmaceutically acceptable salt thereof

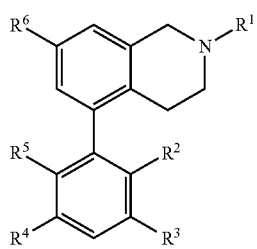

(II)

wherein $R^2$, $R^3$, $R^4$ and $R^5$ are each independently hydrogen, halogen, lower alkyl, —$NH_2$, —$NO_2$, —OH or —CN provided that at least one of $R^2$ and $R^5$ is halogen;

$R^1$ is —$R^7$, or —C(O)$R^7$, wherein $R^7$ is optionally substituted aliphatic, haloalkyl, aryl, heteroaryl, alkylaryl, alkylheteroaryl, carbocycle or heterocycle; and $R^6$ is hydrogen, —$NO_2$, —$NH_2$, —NHC(O)$R^8$, —C(O)NHR$^8$ or —NHS(O)$_2R^8$, wherein $R^8$ is optionally substituted aliphatic (e.g. alkyl), alkylaryl, alkylheteroaryl, aryl, heteroaryl, carbocycle or heterocycle (such as aryl or cycloalkyl). $R^8$ is preferably optionally substituted alkyl, cycloalkyl or aryl.

In certain embodiments, $R^2$, $R^3$, $R^4$ and $R^5$ are each independently hydrogen or halogen, provided that at least one of $R^2$ and $R^5$ is halogen.

In certain embodiments, $R^3$ and $R^4$ are hydrogen.

In certain embodiments, one of $R^2$ and $R^5$ is halogen, preferably chlorine. Preferably, the other of $R^2$ and $R^5$ is hydrogen. In alternative embodiments, both of $R^2$ and $R^5$ are halogen, preferably chlorine.

In some embodiments, where $R^1$ is —$R^7$, $R^7$ is optionally substituted alkylaryl or alkylheteroaryl.

In some embodiments, $R^1$ is benzyl. Alternatively, $R^1$ may be C(O)$R^7$, wherein $R^7$ is alkyl or haloalkyl (for example —$CF_3$ or —$CH_2CH_2CH_3$), or substituted or unsubstituted aryl.

In some embodiments, $R^6$ is not hydrogen.

In some embodiments, $R^6$ is —$NO_2$, —NHS(O)$_2R^8$ or —NHC(O)$R^8$, preferably —$NO_2$ or —NHC(O)$R^8$, more preferably —NHC(O)$R^8$. $R^8$ may be $C_{4-12}$ alkyl, preferably $C_{4-6}$ alkyl, preferably butyl, more preferably n-butyl.

The values described above for $R^1$, $R^2$, $R^3$, $R^4$, $R^5$, $R^6$, $R^7$ and $R^8$ may be present in any combination thereof in compounds of formula (II).

In certain particular embodiments, the compound of formula (II) is selected from:

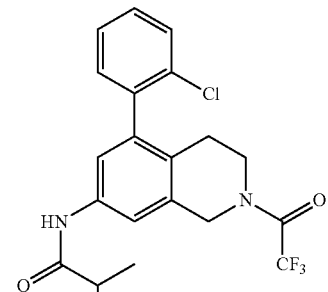

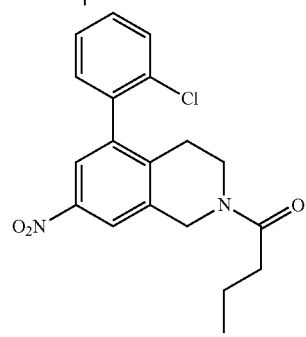

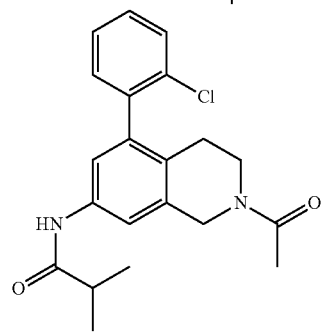

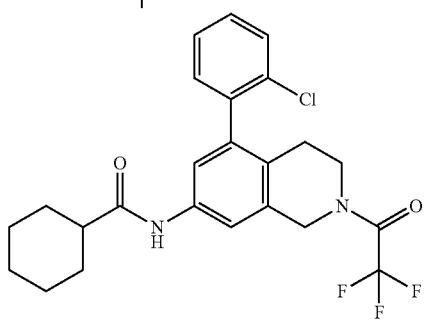

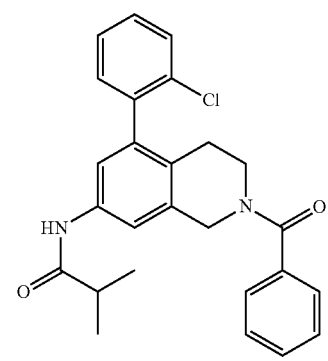

-continued

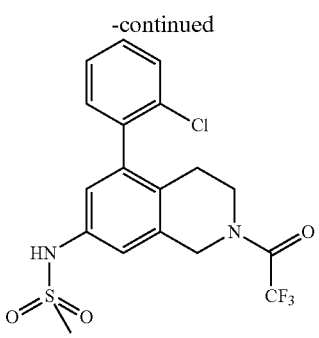

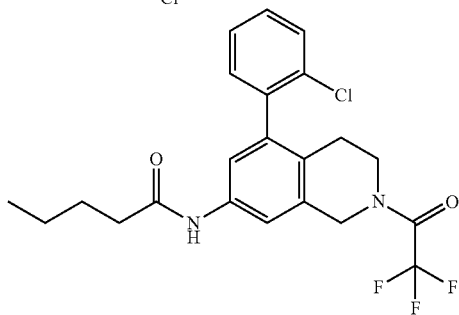

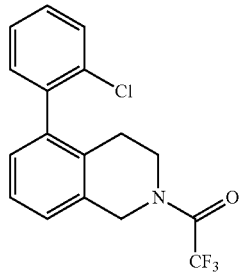

In a second aspect, the invention provides a compound of Formula (III), or a pharmaceutically acceptable salt thereof, (III)

wherein $R^{13}$ is $NR^{14}C(O)R^{15}$, $C(O)NHR^{15}$ or $NR^{14}S(O)_2R^{15}$, wherein $R^{14}$ is hydrogen or alkyl (preferably methyl), and $R^{15}$ is optionally substituted aliphatic (e.g. alkyl), alkylaryl, alkylheteroaryl, aryl, heteroaryl, carbocycle or heterocycle; and $R^2$, $R^3$, $R^4$ and $R^5$ are each independently hydrogen, halogen, lower alkyl, —$NH_2$, —$NO_2$, —OH or —CN, provided that at least one of $R^2$ and $R^5$ is halogen.

In certain embodiments, $R^2$, $R^3$, $R^4$ and $R^5$ are each independently hydrogen or halogen, provided that at least one of $R^2$ and $R^5$ is halogen.

In certain embodiments, $R^3$ and $R^4$ are hydrogen.

In certain embodiments, one of $R^2$ and $R^5$ is halogen, preferably chlorine. Preferably, the other of $R^2$ and $R^5$ is hydrogen. In alternative embodiments, both of $R^2$ and $R^5$ are halogen, preferably chlorine.

In some embodiments, $R^{15}$ is alkyl or substituted or unsubstituted aryl.

In some embodiments, $R^{13}$ is $NHC(O)R^{15}$. In other embodiments, $R^{13}$ is $C(O)NHR^{15}$. $R^{15}$ may be $C_{4-6}$ alkyl, preferably butyl, more preferably n-butyl.

The values described above for $R^2$, $R^3$, $R^4$, $R^5$, $R^{13}$, $R^{14}$ and $R^{15}$ may be present in any combination thereof in compounds of formula (III).

In certain particular embodiments, the compound of formula (III) is selected from:

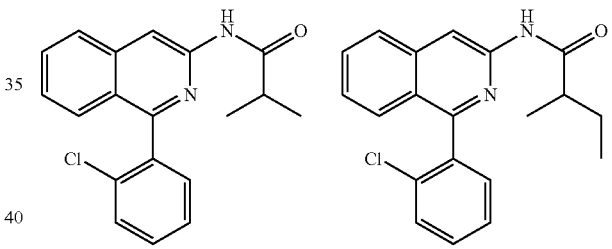

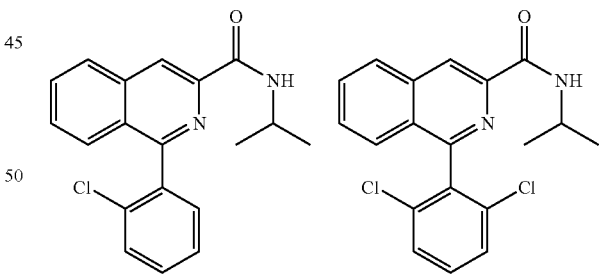

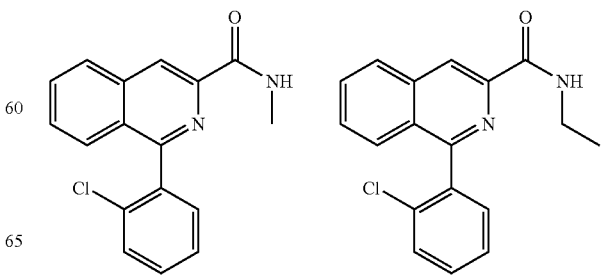

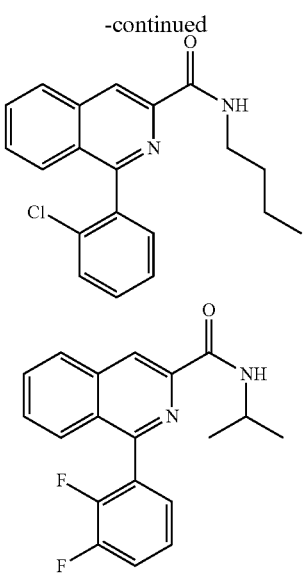

It will be appreciated that the various embodiments described for the tetrahydropyridopyrimidine and tetrahydroisoquinoline compounds of the first aspect of the invention and for the compounds of the second aspect of the invention may be present in combination.

In a third aspect, the invention provides a pharmaceutical composition comprising a compound or a pharmaceutically acceptable salt thereof of any of the first or second aspects of the invention, optionally together with a pharmaceutically acceptable excipient.

In a fourth aspect, the invention provides a compound or a pharmaceutically acceptable salt thereof of any of the first or second aspects of the invention or a pharmaceutical composition of the third aspect of the invention for use in medicine.

In a fifth aspect, the invention provides a compound or a pharmaceutically acceptable salt thereof or a pharmaceutical composition as defined herein for use in preventing and/or treating cancer, an inflammatory disorder, an auto-immune disorder, a neurodegenerative disorder or a connective tissue disorder.

In a sixth aspect, the invention provides a compound or a pharmaceutically acceptable salt thereof or a pharmaceutical composition as defined herein for use as an immunosuppressive agent.

In a seventh aspect, the invention provides a method for preventing and/or treating cancer, an inflammatory disorder, an auto-immune disorder, a neurodegenerative disorder or a connective tissue disorder which comprises administering to a subject in need thereof an effective amount of a compound or pharmaceutically salt thereof or a pharmaceutical composition as defined herein.

In an eighth aspect, the invention provides the use of a compound or a pharmaceutically acceptable salt thereof as defined herein, for the manufacture of a medicament for the prevention and/or treatment of cancer, an inflammatory disorder, an auto-immune disorder, a neurodegenerative disorder or a connective tissue disorder.

In a ninth aspect, the invention provides the use of a compound or a pharmaceutically acceptable salt thereof as defined herein for inducing cell apoptosis.

In a tenth aspect, the invention provides a method for inducing apoptosis of a cell comprising exposing the cell to a compound or pharmaceutically salt thereof or a pharmaceutical composition as defined herein. Said method may be performed in vitro or in vivo.

DESCRIPTION OF THE DRAWINGS

The invention may be put into practice in various ways and a number of specific embodiments will be described by way of example to illustrate the invention with reference to the accompanying figures, in which.

Figure 1:
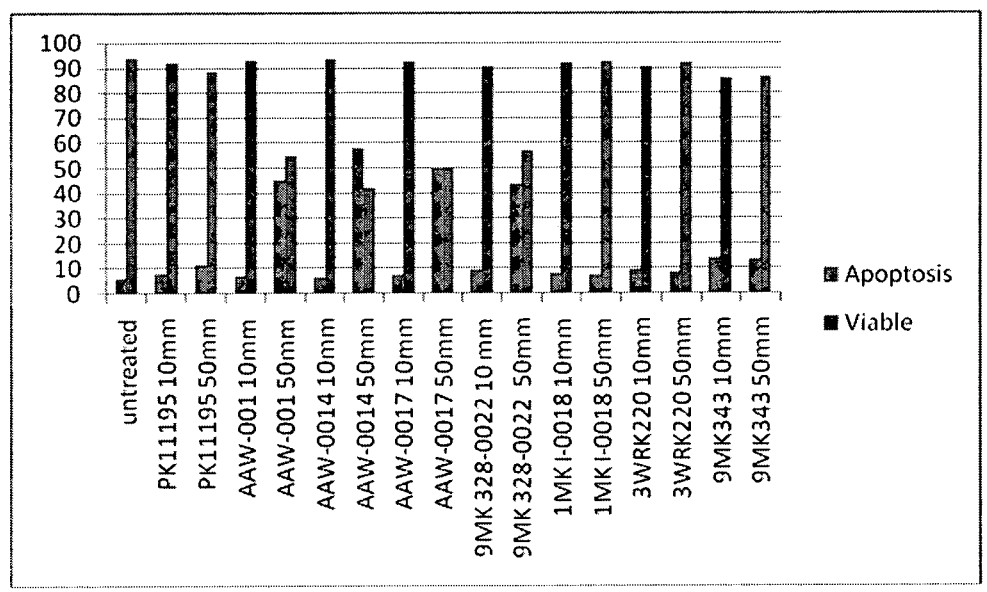
FIG. 1 shows the results of PK11195 and various compounds of the invention on cell viability and apoptosis in the DoHH2 (lymphoma) cell line. $DiOC_6(3)$ flow evaluation of cell viability and levels of apoptosis was carried out at 10 and 50 µm concentrations. For each entry in FIG. 1, % apoptosis is on the left and % viable is on the right.

"mm" as shown in the figures indicates a micromolar concentration.

DETAILED DESCRIPTION OF THE INVENTION

The meanings of terms used in the specification of the present application will be explained below, and the present invention will be described in detail.

The compounds of the present invention are provided for the prevention and/or treatment of cancer, inflammatory disorders, autoimmune disorders, neurodegenerative disorders and/or connective tissue disorders.

Examples of the disorders that can be treated and/or prevented by administration of a compound of the invention are as follows. An example of a "neurodegenerative disorder" is multiple sclerosis. Examples of "autoimmune disorders" include multiple sclerosis, rheumatoid arthritis, autoimmune thrombocytopenia and autoimmune haemolytic anaemia. Examples of "inflammatory disorders" include rheumatoid arthritis and osteoarthritis. Examples of "connective tissue disorders" include systemic lupus and sarcoidosis.

Without wishing to be bound by theory, it is believed that the diseases in which the compounds of the present invention may find greatest application will be in the treatment of cancer. Examples of "cancer" include solid tumours and haematological cancers. Non-limiting examples of solid tumours include lung cancer, colon cancer; breast cancer, liver cancer, pancreatic cancer; bladder cancer; colorectal cancer; prostate cancer; renal cancer, ovarian cancer; cervical cancer; gastric cancer; esophageal cancer; head and neck cancer; melanoma; brain tumours; bone cancer. Non-limiting examples of haematological cancers include leukaemia, lymphoma and myeloma.

Compounds of the invention, when used for preventing or treating a disease, may be administered in an "effective amount". By an "effective amount" it is meant a "therapeutically effective amount", namely an amount of compound sufficient, upon single dose or multiple dose administration, to cause a detectable decrease in disease severity, to prevent advancement of a disease or alleviate disease symptoms beyond that expected in the absence of treatment.

Compounds of the invention are useful for reducing the severity of symptoms of any of the above disorders to be treated. Compounds of the invention are also useful for administration to patients susceptible to, at risk of or suffering from any of the above disorders. Compounds useful for prevention of the above disorders are not required to absolutely prevent occurrence of the disorder in all cases, but may prevent or delay onset of the disorder when administered to a patient susceptible to or at risk of the disorder.

The term "halogen" or "halo" as used herein means fluorine, chlorine, bromine, iodine and the like, preferably fluorine or chlorine, and more preferably chlorine.

The term "aliphatic" as used herein refers to a straight or branched chain hydrocarbon which is completely saturated or contains one or more units of unsaturation. Thus, aliphatic may be alkyl, alkenyl or alkynyl, preferably having 1 to 12 carbon atoms, up to 6 carbon atoms or up to 4 carbon atoms.

The term "alkyl" as used herein refers to a straight or branched chain alkyl group. Preferably, an alkyl group as referred to herein is a $C_{1-12}$ alkyl group. More preferably, an alkyl group as referred to herein is a lower alkyl having 1 to 6 carbon atoms. The alkyl group therefore has 1, 2, 3, 4, 5 or 6 carbon atoms. Specifically, examples of "a lower ($C_{1-6}$) alkyl" include methyl, ethyl, n-propyl, iso-propyl, n-butyl, iso-butyl, sec-butyl, tert-butyl, n-pentyl, 1,1-dimethylpropyl, 1,2-dimethylpropyl, 2,2-dimethylpropyl, 1-ethylpropyl, n-hexyl, 1-ethyl-2-methylpropyl, 1,1,2-trimethylpropyl, 1-ethylbutyl, 1-methylbutyl, 2-methylbutyl, 1,1-dimethylbutyl, 1,2-dimethylbutyl, 2,2-dimethylbutyl, 1,3-dimethylbutyl, 2,3-dimethylbutyl, 2-ethylbutyl, 2-methylpentyl, 3-methylpentyl and the like.

The term "carbocycle" as used herein refers to a saturated or partially unsaturated cyclic group having 3 to 8 ring carbon atoms. A carbocycle is preferably a "cycloalkyl", which as used herein refers to a fully saturated hydrocarbon cyclic group. Preferably, a cycloalkyl group is a $C_3$-$C_6$ cycloalkyl group.

The term "heterocycle" as used herein refers to a saturated or partially unsaturated cyclic group having, in addition to carbon atoms, one or more heteroatoms selected from O, N and S. A heterocycle preferably has 3 to 7 ring atoms.

The term "haloalkyl" as used herein refers to an alkyl group as described above, substituted with one or more halogen atom(s), preferably 1, 2 or 3 halogen atom(s). Preferably, a haloalkyl is a $C_{1-6}$ haloalkyl. Specifically, examples of a "$C_{1-6}$ haloalkyl" include fluoromethyl, difluoromethyl, trifluoromethyl, fluoroethyl, difluoroethyl, trifluoroethyl, chloromethyl, bromomethyl, iodomethyl and the like, preferably trifluoromethyl.

The term "aryl" as used herein refers to a monocyclic or bicyclic aromatic ring having 6 to 10 carbon atoms. Preferably, an aryl is phenyl.

The term "heteroaryl" as used herein refers to a monocyclic or bicyclic aromatic ring system having from 5 to 10 ring atoms, at least one ring atom being a heteroatom selected from O, N or S.

An aryl, heteroaryl, carbocycle or heterocycle group as referred to herein may be unsubstituted or may be substituted by one or more substituents independently selected from the group consisting of halo, aliphatic, alkoxy, alkylamino (monoalkylamino or dialkylamino), —$NH_2$, —$NO_2$, —OH, —COOH, —CN, hydroxyalkyl, alkylcarbonyloxy, alkoxycarbonyl, alkylcarbonyl or alkylsulfonylamino. Preferred substituents include halo, lower alkyl, —$NH_2$, $NO_2$, —OH or —CN, preferably halo.

An aliphatic group or a haloalkyl group as referred to herein may be unsubstituted or may independently be substituted with aryl, heteroaryl, carbocycle, heterocycle or with any one or more of the substituents listed above for aryl, heteroaryl, carbocycle or heterocycle groups.

The terms "alkylaryl" and "alkylheteroaryl" as used herein refers to an alkyl group as defined above substituted with an aryl or heteroaryl group as defined above. The alkyl component of an "alkylaryl" or "alkylheteroaryl" group may be substituted with any one or more of the substituents listed above for an aliphatic group and the aryl or heteroaryl component of an "alkylaryl" or "alkylheteroaryl" group may be substituted with any one or more of the substituents listed above for aryl, heteroaryl, carbocycle or heterocycle groups. Preferably, alkylaryl is benzyl.

In compounds of the invention, one or more asymmetric carbon atoms may be present. For such compounds, the invention is understood to include all isomeric forms (e.g. enantiomers and diastereoisomers) of the compounds as well as mixtures thereof, for example racemic mixtures.

The compounds of the invention may be provided as the free compound or as a suitable salt or hydrate thereof. Salts should be those that are pharmaceutically acceptable and salts and hydrates can be prepared by conventional methods, such as contacting a compound of the invention with an acid or base whose counterpart ion does not interfere with the intended use of the compound. Examples of pharmaceutically acceptable salts include hydrohalogenates, inorganic acid salts, organic carboxylic acid salts, organic sulfonic acid salts, amino acid salt, quaternary ammonium salts, alkaline metal salts, alkaline earth metal salts and the like.

The compounds of the invention can be provided as a pharmaceutical composition. The pharmaceutical composition may additionally comprise a pharmaceutically acceptable excipient for example a pharmaceutically acceptable carrier and/or a pharmaceutically acceptable diluent. Suitable carriers and/or diluents are well known in the art and include pharmaceutical grade starch, mannitol, lactose, magnesium stearate, sodium saccharin, talcum, cellulose, glucose, sucrose (or other sugar), magnesium carbonate, gelatin oil, alcohol, detergents, emulsifiers or water (preferably sterile).

A pharmaceutical composition may be provided in unit dosage form, will generally be provided in a sealed container and may be provided as part of a kit. Such a kit would normally (although not necessarily) include instructions for use. It may include a plurality of said unit dosage forms.

A pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with a carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes. Pharmaceutical compositions adapted for rectal administration may be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulizers or insufflators. Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts, buffers, coating agents or antioxidants. They may also contain an adjuvant and/or therapeutically active agents in addition to the substance of the present invention.

Dosages of the substance of the present invention can vary between wide limits, depending upon a variety of factors including the disease or disorder to be treated, the age, weight and condition of the individual to be treated, the route of administration etc. and a physician will ultimately determine appropriate dosages to be used. Typically, however, the dosage adopted for each route of administration when a compound of the invention is administered to adult humans is 0.001 to 500 mg/kg. Such a dosage may be given, for example, from 1 to 5 times daily by bolus infusion, infusion over several hours and/or repeated administration. The compositions may be administered in conjunction with one or more other therapeutically active agents, especially those effective for treating cancers (i.e. a chemotherapeutic agent). Another chemotherapeutic agent may be, for example, mitoxantrone, Vinca alkaloids, such as vincristine and vinblastine, anthracycline antibiotics such as daunorubicin and doxorubicin, alkylating agents such as chlorambucil and melphalan, taxanes such as paclitaxel, anti-folates such as methotrexate and tomudex, epipodophyllotoxins such as etoposide, camptothecins such as irinotecan and its active metabolite SN-38 and DNA methylation inhibitors. The other active compound (s) may be incorporated in the same composition as the compounds of the present invention or they may be administered alongside the compounds of the present invention, e.g. simultaneously or sequentially. Thus, the invention provides a kit of parts comprising a compound of the invention and another chemotherapeutic agent, optionally with instructions for use.

EXAMPLES

The following examples of the invention are provided to aid understanding of the invention but should not be taken to limit the scope of the invention. The table below sets out isoquinoline, tetrahydroisoquinoline and tetrahydropyridopyrimidine exemplary compounds of the invention as well as certain compounds which are provided as reference examples.

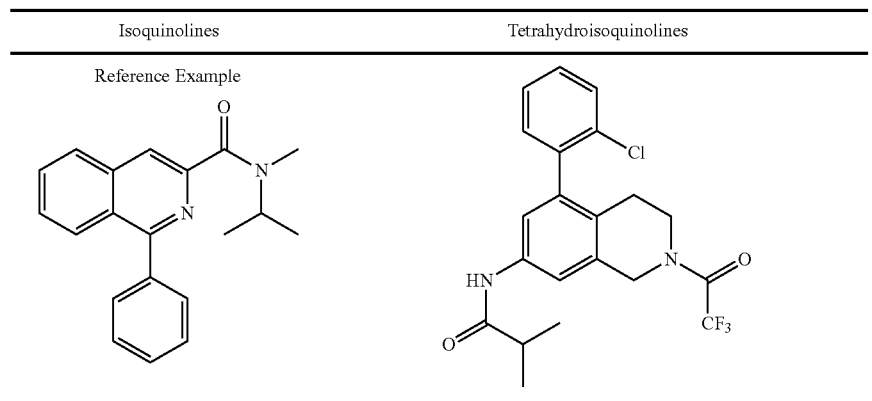

-continued
| Reference Example | Reference Example |
|---|---|
| 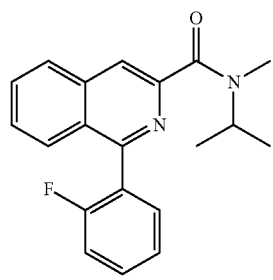<br>MW-322.38<br>CO-AA W0005 | 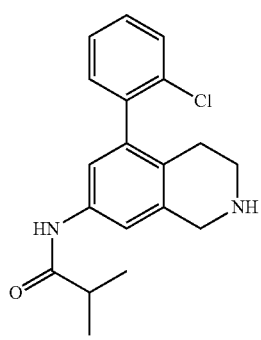<br>MW-328.84<br>CO-AA W0003 |
| 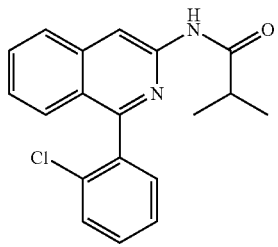<br>MW-324.81<br>CO-AA W0007 | 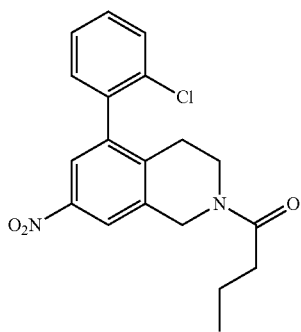 [SMILES: CCCC(=O)N1CCc2c(cc([N+](=O)[O-])cc2-c2ccccc2Cl)C1]<br>MW-358<br>CO-AA W00017 |
| 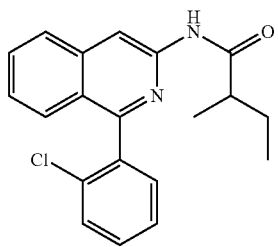 [SMILES: CCC(C)C(=O)Nc1cc2ccccc2c(-c2ccccc2Cl)n1]<br>MW-338.84<br>CO-AA W0008 | 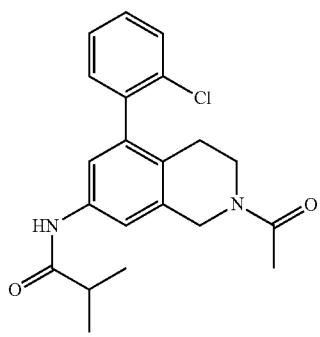 [SMILES: CC(=O)N1CCc2c(cc(NC(=O)C(C)C)cc2-c2ccccc2Cl)C1]<br>MW-370.88<br>CO-AA W00024<br>8MK336-I |
| 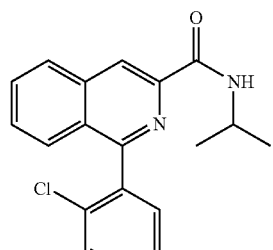<br>MW-338.84<br>CO-AA W0009 | 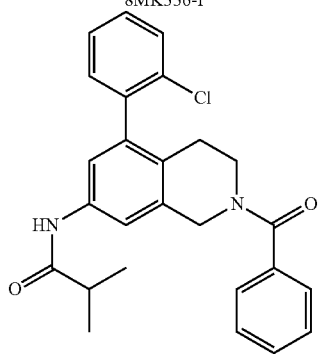<br>MW-432.95<br>CO-AA W00025<br>8MK336-II |

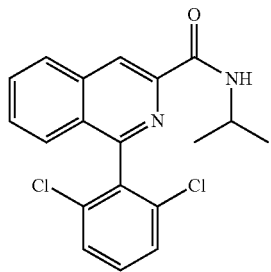 [SMILES: CC(C)NC(=O)c1cc2ccccc2c(-c2c(Cl)cccc2Cl)n1]
MW-371
CO-AA W00018
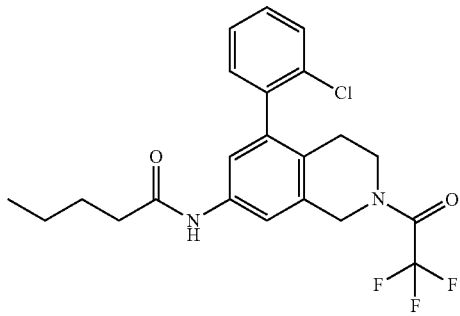 [SMILES: CCCCC(=O)Nc1cc2c(c(-c3ccccc3Cl)c1)CCN(C(=O)C(F)(F)F)C2]
CO-AA W00030
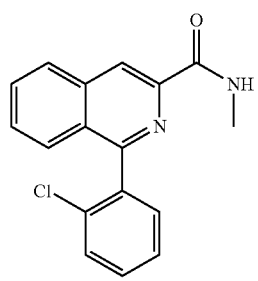 [SMILES: CNC(=O)c1cc2ccccc2c(-c2ccccc2Cl)n1]
MW-296.76
CO-AA W00020
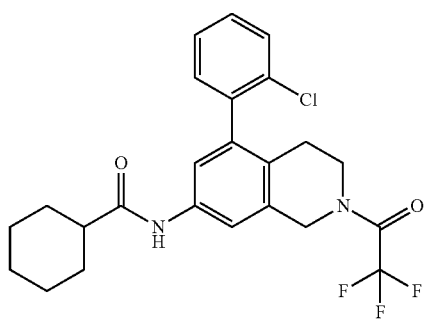 [SMILES: O=C(Nc1cc2c(c(-c3ccccc3Cl)c1)CCN(C(=O)C(F)(F)F)C2)C1CCCCC1]
CO-AA W00031
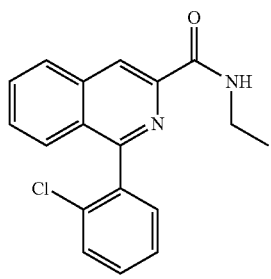 [SMILES: CCNC(=O)c1cc2ccccc2c(-c2ccccc2Cl)n1]
MW-310.78
CO-AA W00021
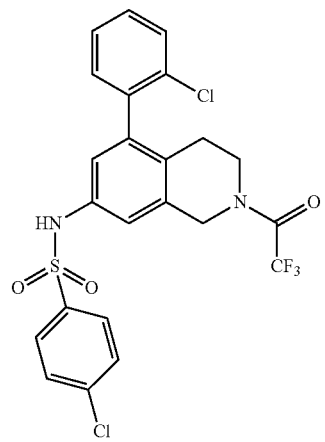 [SMILES: O=C(N1CCc2c(cc(NS(=O)(=O)c3ccc(Cl)cc3)cc2-c2ccccc2Cl)C1)C(F)(F)F]
CO-AA W00034
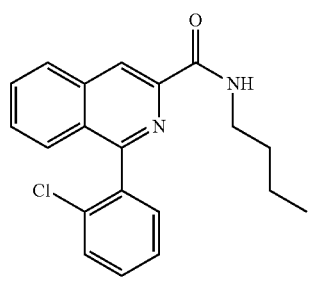 [SMILES: CCCCNC(=O)c1cc2ccccc2c(-c2ccccc2Cl)n1]
MW-338.84
CO-AA W00022
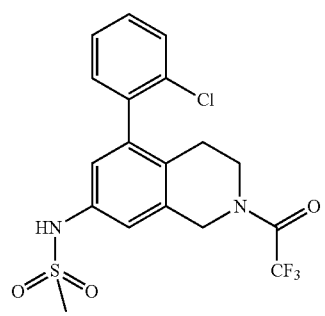 [SMILES: CS(=O)(=O)Nc1cc2c(c(-c3ccccc3Cl)c1)CCN(C(=O)C(F)(F)F)C2]

-continued
Reference Example
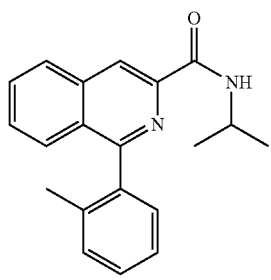
CO-AA W00023
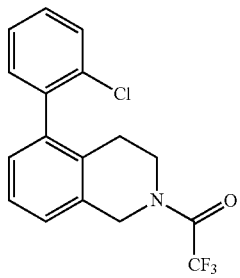 [SMILES: O=C(N1CCc2c(cccc2-c2ccccc2Cl)C1)C(F)(F)F]
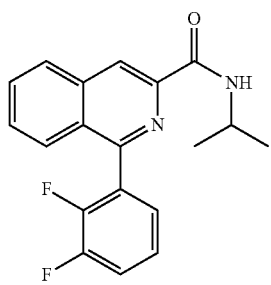 [SMILES: CC(C)NC(=O)c1cc2ccccc2c(-c2cccc(F)c2F)n1]
MW-430
9MK343
| Tetrahydropyridopyrimidines |
|---|
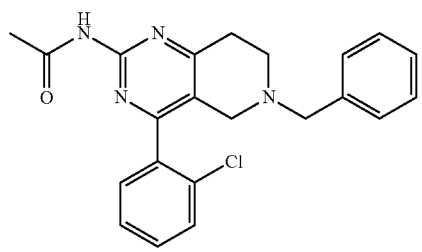 [SMILES: CC(=O)Nc1nc2c(c(-c3ccccc3Cl)n1)CN(Cc1ccccc1)CC2]
MW-392
CO-AA W00011
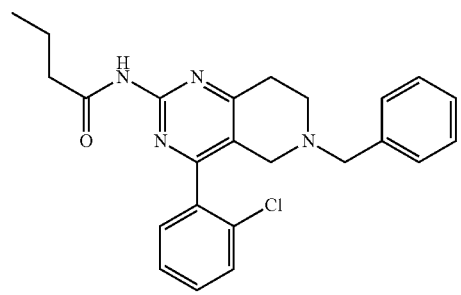 [SMILES: CCCC(=O)Nc1nc2c(c(-c3ccccc3Cl)n1)CN(Cc1ccccc1)CC2]
MW-420
CO-AA W00012

-continued
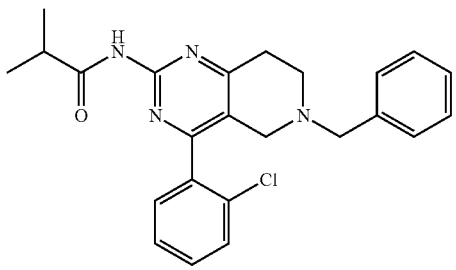 [SMILES: CC(C)C(=O)Nc1nc2c(c(-c3ccccc3Cl)n1)CN(Cc1ccccc1)CC2]
MW-420
CO-AA W00013
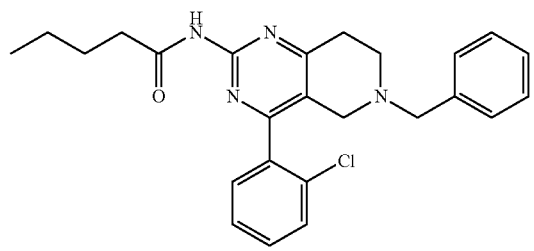 [SMILES: CCCCC(=O)Nc1nc2c(c(-c3ccccc3Cl)n1)CN(Cc1ccccc1)CC2]
MW-434
CO-AA W00014
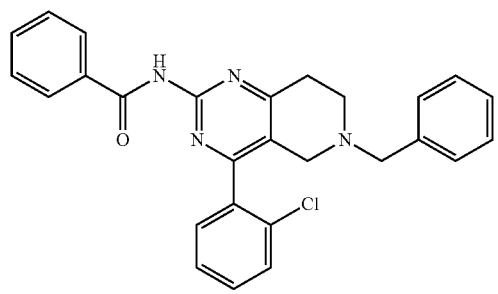 [SMILES: O=C(Nc1nc2c(c(-c3ccccc3Cl)n1)CN(Cc1ccccc1)CC2)c1ccccc1]
MW-454
CO-AA W00015
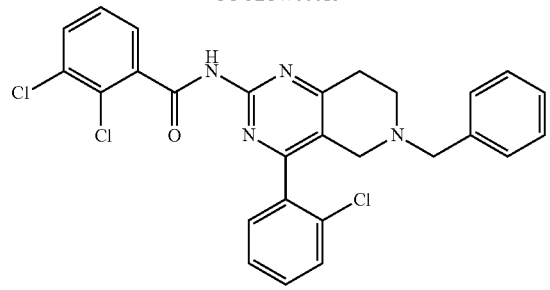 [SMILES: O=C(Nc1nc2c(c(-c3ccccc3Cl)n1)CN(Cc1ccccc1)CC2)c1cccc(Cl)c1Cl]
MW-522
CO-AA W00016
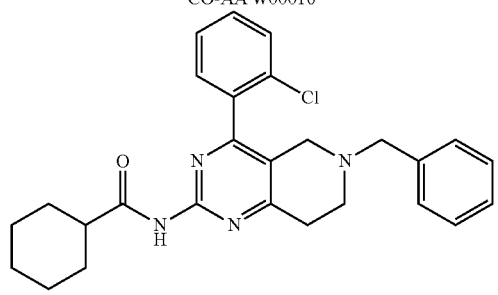
CO-AA W00032

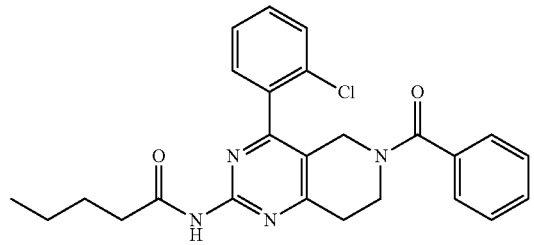 [SMILES: CCCCC(=O)Nc1nc2c(c(-c3ccccc3Cl)n1)CN(C(=O)c1ccccc1)CC2]

CO-AA W00033

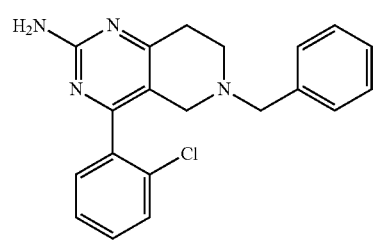

MW 350.5
3WRK220

Reference Example

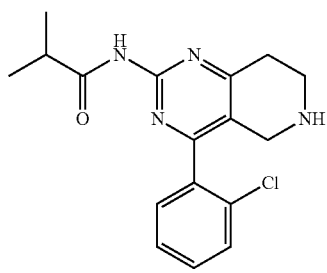

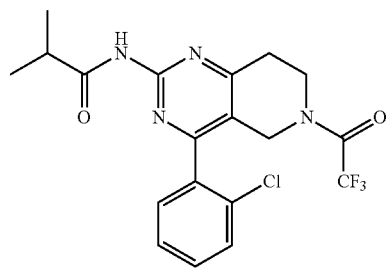

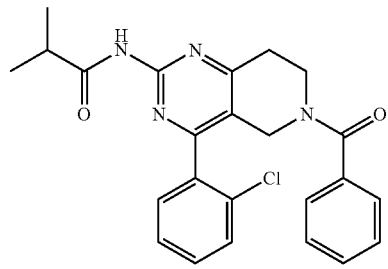

For compounds of the tetrahydroisoquinoline series of formula (II), and exemplified by certain compounds set out in the table above, side chain $R^1$ has been determined to produce compounds with good apoptotic activity. Similarly, for compounds of the tetrahydropyridopyrimidine serried of formula (I) and exemplified by certain compounds set out in the table above, the side chain $R^9$ has been determined to produce compounds with good apoptotic activity. Increase in side chain lipophilicity has been determined to enhance activity. For compounds of the isoquinoline series of formula (III), and exemplified by certain compounds set out in the table above, increase in lipophilicity of side chain $R^{15}$ has been determined to enhance activity. Side chain lipophilicity increases lipid binding capability, which is thought to be important for internalisation of the compound into the inner mitochchondria in order to exert its effect. The membrane of the mitochondria contains the lipid rafts that permit binding and internalisation of compounds with this property.

General Reaction Scheme for the Synthesis of Tetrahydroisoquinolines

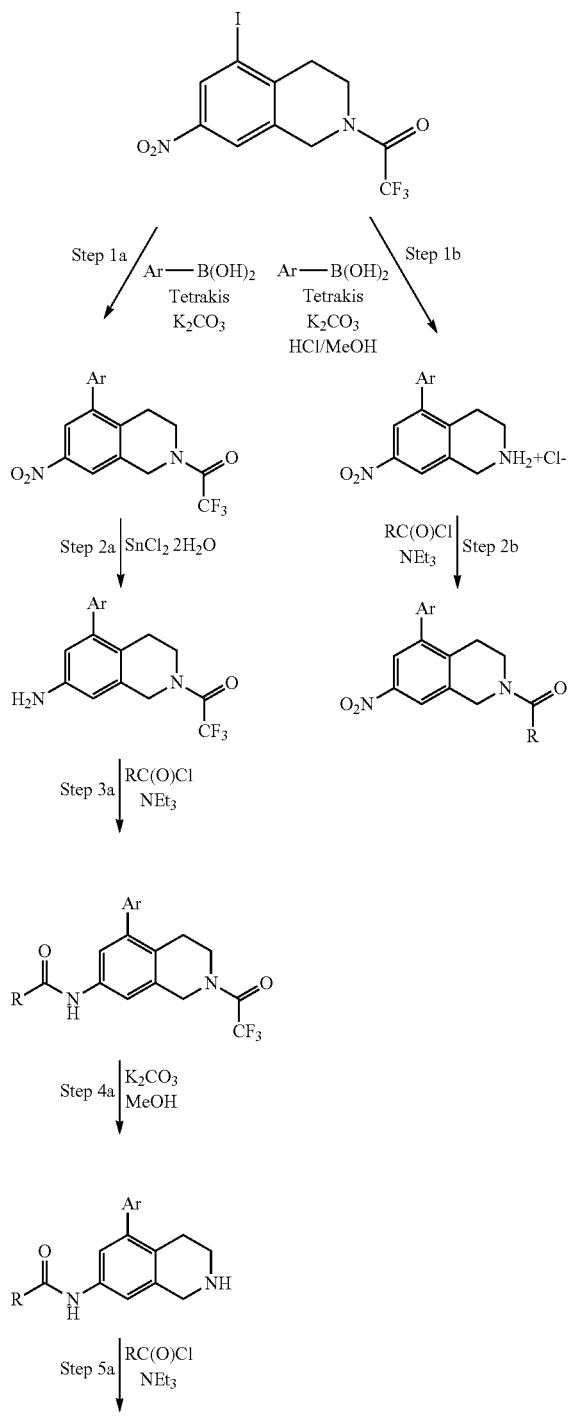

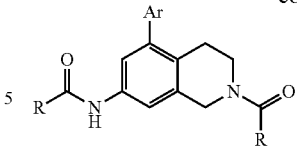

The starting material in the above general reaction scheme, 2,2,2-trifluoro-1-(5-iodo-7-nitro-3,4-dihydro-1H-isoquinolin-2-yl)-ethanone, can be prepared by the route set out below. Following this, the reaction scheme will be further illustrated by synthesis of compounds CO-AAW0001, 17, 24, 25, 30, 31 and 34.

Synthesis of 2,2,2-trifluoro-1-(5-iodo-7-nitro-3,4-dihydro-1H-isoquinolin-2-yl)-ethanone

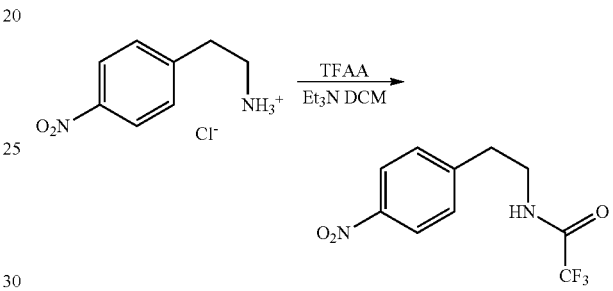

Synthesis of 2,2,2-trifluoro-N-[2-(4-nitro-phenyl)-ethyl]-acetamide 2-(4-Nitro-phenyl)-ethylamine hydrochloride (19.7 g, 97.28 mmoles) was suspended in dichloromethane (300 mls) to which was added triethylamine (26.91 mls, 194.5 mmoles) and the solution was chilled to 0° C. in ice. Trifluoroacetic anhydride (55.2 mls, 389 mmoles) was then added dropwise over 1 hour whilst under nitrogen. The solvent was removed in 'vacuo' and the resulting yellow oil pipetted into ice water (200 mls) and the solid filtered off and dried in a vacuum oven to leave a yellow solid (25.6 g, 100% yield). LC-MS (retention 3.46 mins).

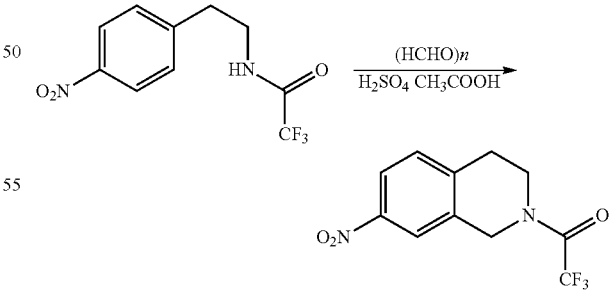

Synthesis of 2,2,2-trifluoro-1-(7-nitro-3,4-dihydro-1H-isoquinolin-2-yl)-ethanone A solution of concentrated sulphuric acid (148 mls) and glacial acetic (99 mls) was prepared and allowed to cool to room temperature. The acid solution was rapidly stirred whilst a mixture of 2,2,2-Trifluoro-N-[2-(4-nitro-phenyl)-ethyl]-acetamide (25.91 g, 98.9 mmoles) and paraformaldehyde (4.74 g, 158.2 mmoles) were added portionwise. The mixture was stirred at room temperature for 18 hours. The pale yellow solid was then filtered and dried in a vacuum oven (24.33 g, 90% yield). LC-MS (retention, 3.65 mins).

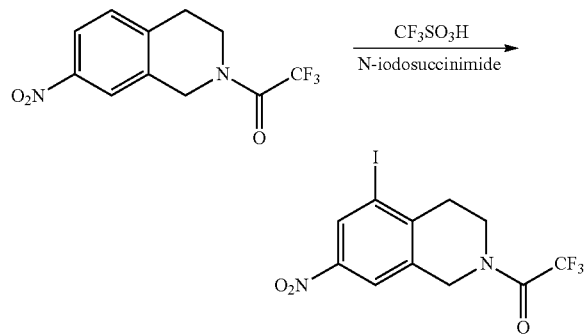

Synthesis of 2,2,2-trifluoro-1-(5-iodo-7-nitro-3,4-dihydro-1H-isoquinolin-2-yl)-ethanone Trifluoromethane sulphonic acid (78 mls, 876 mmoles) was added to a 500 ml round bottomed flask to which was added 2,2,2-trifluoro-1-(7-nitro-3,4-dihydro-1H-isoquinolin-2-yl)-ethanone, 1OA43, 24 g, 87.6 moles) in portions over 30 minutes. The dark viscous solution was then cooled in an ice-bath and iodosuccinimide (19.7 g, 87.6 mmoles) was added over 1 hour and the reaction left overnight. Starting material was still present in the reaction mixture so further portion of iodosuccinimide (11.82 g, 52.56 mmoles) was added over 30 minutes and the solution stirred for 24 hours. The reaction mixture was then slowly poured into ice-water producing a brown solid. This mixture was then repeatedly extracted with dichloromethane (4×100 mls) and the organic solution was washed with aqueous sodium thiosulphate (3×200 mls, 10%) followed by water (3×200 mls) and the organic layer was then dried over anhydrous magnesium sulphate. Removal of the solvent left a beige solid which was re-crystallized from ethylacetate and hexane (21 g, 60% yield). LC-MS (retention 4.0 mins, M+H 401).

Synthesis of CO-AAW0001

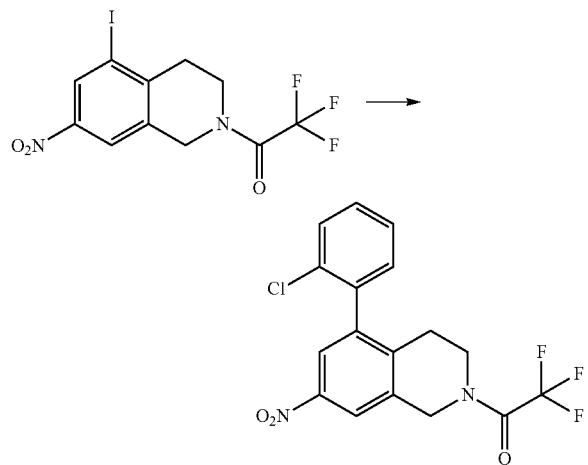

Synthesis of 1-[5-(2-chloro-phenyl)-7-nitro-3,4-dihydro-1H-isoquinolin-2-yl]-2,2,2-trifluoro-ethanone 2,2,2-Trifluoro-1-(5-iodo-7-nitro-3,4-dihydro-1H-isoquinolin-2-yl)-ethanone (1MK1, 750 mgs, 1.88 mmoles) was dissolved in toluene (25 mls) and 2-chlorophenyl boronic acid (352 mg, 2.25 mmoles), anhydrous potassium carbonate (311 mg, 2.25 mmoles) and finally palladium tetrakis catalyst (111 mg, 0.099 mmoles, 5 mol %) was added. The reaction mixture was flushed with nitrogen and heated to 95° C. overnight. Starting material was still present therefore further 2-chlorophenyl boronic acid (88 mg, 0.56 mmoles), potassium carbonate (78 mg, 0.56 mmoles) and catalyst (28 mg, 0.025 mmoles) were added and the reaction continued for a further 2 hours. The reaction was then cooled and filtered through a pad of Celite. The filtrate was washed with saturated sodium bicarbonate solution (25 mls), water (25 mls) and brine (25 mls). The organic layer was dried over anhydrous magnesium sulphate, filtered and evaporated to give an oily residue. The oil was triturated with ether followed by isopropanol:hexane 1:1. The dark yellow solid (724 mg, 100% yield) was used without further purification. LC-MS (retention, 4.2 mins M+H 386).

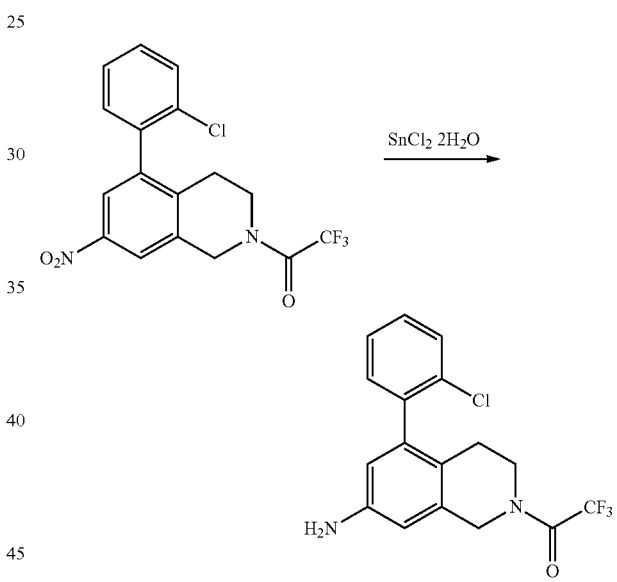

Synthesis of 1-[7-amino-5-(2-chloro-phenyl)-3,4-dihydro-1H-isoquinolin-2-yl]-2,2,2-trifluoro-ethanone 1-[5-(2-Chloro-phenyl)-7-nitro-3,4-dihydro-1H-isoquinolin-2-yl]-2,2,2-trifluoro-ethanone (760 mg, 1.97 mmoles) was dissolved in methanol (10 mls) and stannous chloride dihydrate (2.23 g, 9.87 mmoles) was added. The yellow coloured reaction mixture was heated to 65° C. for 2 hours, evaporated and partitioned between ethylacetate (50 mls) and water (50 mls). The solution was then basified by the addition of potassium hydroxide solution (10%) to a pH 11-12. The whole mixture was then filtered through a Celite pad and washed with ethylacetate (20 mls), water (20 mls) and brine (40 mls) and finally dried over anhydrous magnesium sulphate. After filtration and evaporation the yellow oil was triturated with ether (2×25 mls) and hexane (25 mls) to give an oily solid (500 mg, 60% yield). LC-MS (retention 3.60, M+H 356).

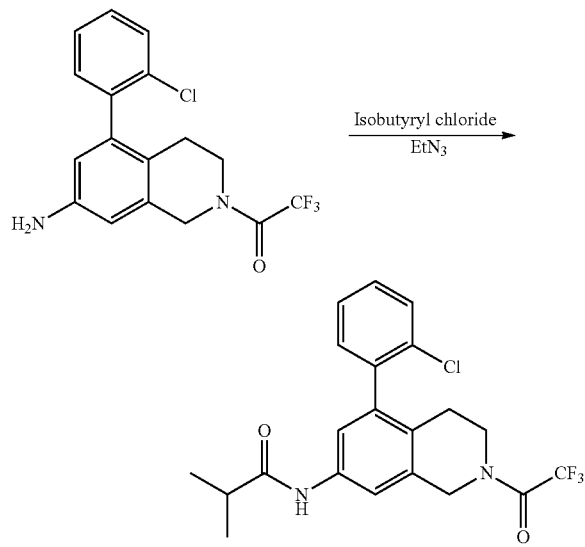

Synthesis of N-[5-(2-chloro-phenyl)-2-(2,2,2-trifluoro-acetyl)-1,2,3,4-tetrahydro-isoquinolin-7-yl]-isobutyramide (CO-AAW0001)

To 1-[7-amino-5-(2-chloro-phenyl)-3,4-dihydro-1H-isoquinolin-2-yl]-2,2,2-trifluoro-ethanone (710 mg, 2 mmoles) was added dimethylacetamide (10 mls) in a round bottomed flask (100 ml). To this solution was added isobutyryl chloride (313 μl, 3 mmoles) followed by triethylamine (416 μl. 3 mmoles). The flask was flushed with nitrogen and stirred at room temperature overnight. Further isobutyryl chloride (104 μl, 1.0 mmole) and triethylamine (138 μl, 1.0 mmole) and the reaction stirred for 2 hours. Ethylacetate (50 ml) was added to the reaction mixture which was then washed with water (50 ml). The organic layer was then further washed with water (3×30 ml), brine (30 ml) and then the organic layer was dried over anhydrous magnesium sulphate. After filtration and evaporation, a brown oil (900 mg) resulted which was triturated three times in hexane to leave a dark yellow solid. This solid was chromatographed on silica gel (20 g) and eluted with hexane and ethylacetate (8:2). Pure fractions were pooled and evaporated to yield product (123 mg, 95% pure). The impure fractions were pooled and purified by reverse phase chromatography (Genesis $C_{18}$, 4 μm, 27.5 cm×1.25 cm) running a gradient of 95% water (0.1% trifluoroacetic acid) 5% acetonitrile (0.1% trifluoroactic acid) to 95% acetonitrile and 5% water over 20 minutes, to give product (166 mg, 95% pure). Both samples were combined (270 mg, 32% yield, CO-AAW0001). LC-MS (retention, 6.35 min, M+H 426).

Synthesis of CO-AAW00017

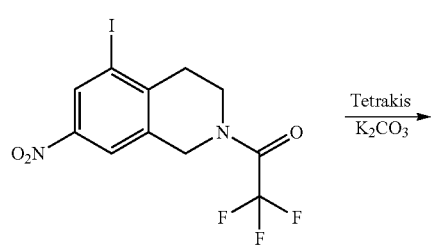

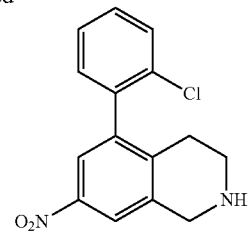

Synthesis of 5-(2-chlorophenyl)-7-nitro-1,2,3,4-tetrahydroisoquinoline 2,2,2-Trifluoro-1-(5-iodo-7-nitro-3,4-dihydro-1H-isoquinolin-2-yl)ethanone (0.8 g, 2 mmoles) and 2-chlorophenyl boronic acid (0.31 g, 2 mmoles) were stirred with an acetonitrile water mixture (50:50, 28 mls). Anhydrous potassium carbonate (0.55 g, 4 mmoles) was then added under a stream of nitrogen. To this solution was then added palladium tetra (triphenyl phosphine) (tetrakis, 0.12 g, catalytic) and the solution heated (95° C.) for three hours. The reaction mixture was cooled to room temperature and water (10 mls) added followed by dichloromethane (3×60 mls), the combined dichloromethane extracts were washed with brine (20 mls) and dried over magnesium sulphate. The solution was then filtered and evaporated to leave an orange gum which was then dissolved in ether (20 mls) to which was added HCl/MeOH (4M) dropwise to afford a beige precipitate which was collected and dried (0.62 g, 95%, 90% pure).

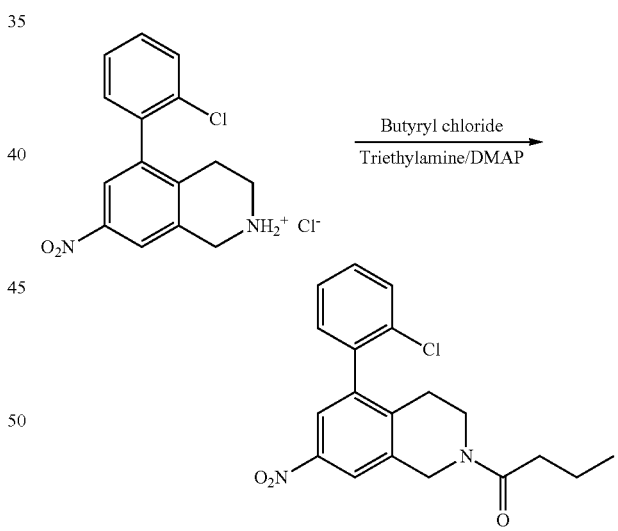

Synthesis of 1-[5-(2-chlorophenyl)-7-nitro-1,2,3,4-tetrahydroisoquinolin-2-yl]butan-1-one (CO-AAW00017)

5-(2-chlorophenyl)-7-nitro-1,2,3,4-tetrahydroisoquinoline (0.065 g, 0.2 mmoles) was dissolved in anhydrous dimethylacetamide (1 ml) followed by the addition of triethylamine (0.068 mls) and butyryl chloride (0.0253 mls, 0.24 mmoles) followed finally by N,N-dimethylamino pyridine (catalytic amount). The reaction was left stirring at room temperature for 2.5 hours and the solution purified by automated C18 HPLC purification (0.0336 g, 47% yield, 100% pure, CO-AAW00017).

Synthesis of CO-AAW00030

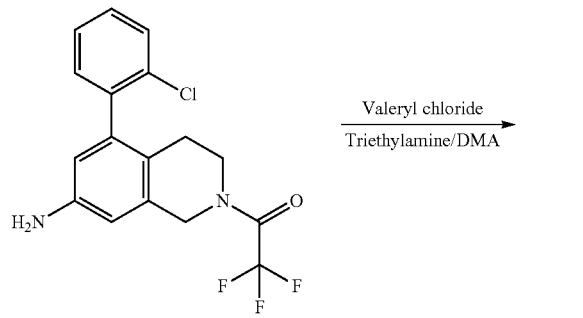

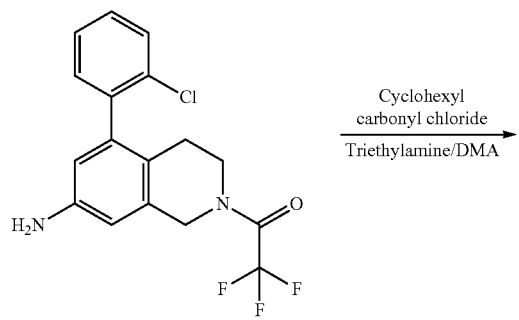

Synthesis of pentanoic acid [5-(2-chlorophenyl)-2-(2,2,2-trifluoro-acetyl)-1,2,3,4-tetrahydro-isoquinolin-7-yl]amide (CO-AAW00030)

1-[7-amino-5-(2-chloro-phenyl)-3,4-dihydro-1H-isoquinolin-2-yl]-2,2,2-trifluoro-ethanone (71 mgs, 0.2 mmoles) was dissolved in anhydrous dimethylacetamide (1 ml) to which was added valeryl chloride (36 ul, 0.3 mmoles) and finally triethylamine (41.6 ul, 0.3 mmoles). The vial was flushed with nitrogen and stirred at room temperature overnight. The product was twice purified by semi-preparative $C_{18}$ HPLC (11.5 mgs, 13.1% yield, 94% pure, CO-AAW00030).

Synthesis of CO-AAW00031

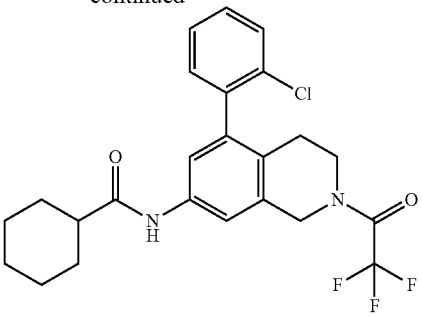

Synthesis of cyclohexane carboxylic acid [5-(2-chlorophenyl)-2-(2,2,2-Trifluoro-acetyl)-1,2,3,4-tetrahydro-isoquinolin-7-yl]amide (CO-AAW00031)

1-[7-amino-5-(2-chloro-phenyl)-3,4-dihydro-1H-isoquinolin-2-yl]-2,2,2-trifluoro-ethanone (71 mgs, 0.2 mmoles) was dissolved in anhydrous dimethylacetamide (1 ml) to which was added cyclohexyl carbonyl chloride (40 ul, 0.3 mmoles) followed by triethylamine (41.6 ul, 0.3 mmoles) and the solution flushed with nitrogen and left stirring overnight. The product was purified by semi-preparative $C_{18}$ HPLC (9.4 mgs, 10.2% yield, 100% pure, CO-AAW00031).

Synthesis of CO-AAW00034

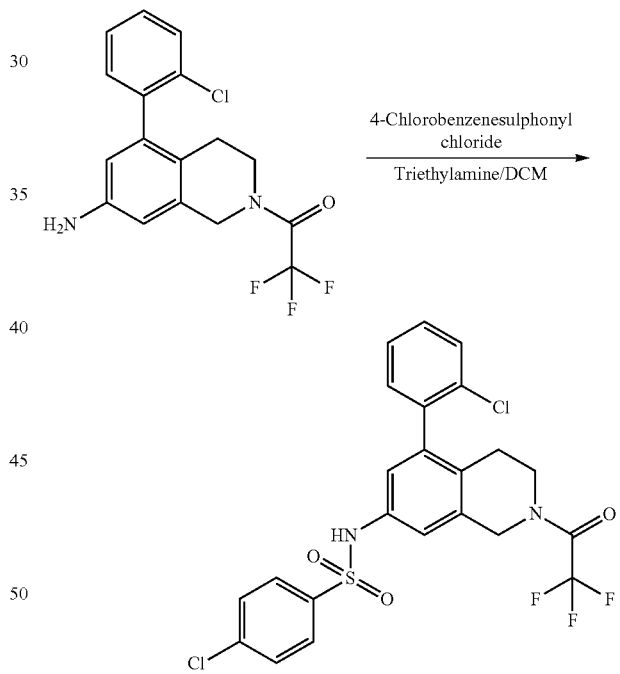

Synthesis of 4-chloro-N-[5-(2-chloro-phenyl)-2-(2,2,2-trifluoro-acetyl)-1,2,3,4-tetrahydro-isoquinolin-7-yl]-benzenesulphonamide (CO-AAW00034)

1-[7-amino-5-(2-chloro-phenyl)-3,4-dihydro-1H-isoquinolin-2-yl]-2,2,2-trifluoro-ethanone (80 mgs, 0.2 mmoles) was stirred in dichloromethane (12 mls) and triethylamine (80 ul, 0.58 mmoles) was added, followed by 4-chlorobenzenesulphonyl chloride (75 mgs, 0.36 mmoles). The reaction was flushed with nitrogen and left stirring at room temperature overnight. The reaction was purified by semi-preparative $C_{18}$ HPLC (47 mgs, 44% yield, 100% pure, CO-AAW00034).

Synthesis of CO-AAW00024

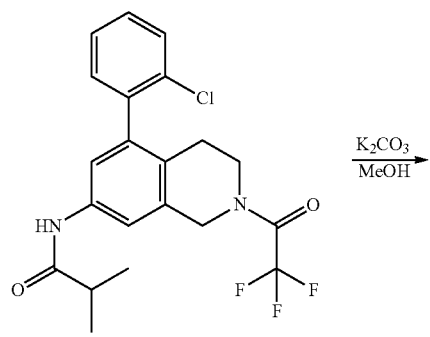

Synthesis of N-[2-Acetyl-5-(2-chloro-phenyl)-1,2,3,4-tetrahydro-isoquinolin-7-yl]2-methylpropanamide (CO-AAW00024)

CO-AAW0003 (39 mgs, 0.12 mmoles) was dissolved in anhydrous dimethylacetamide (1 ml) followed by the addition of triethylamine (20 ul, 0.144 mmols) and acetyl chloride (10.3 ul, 0.144 mmoles). The reaction was then left stirring at room temperature for 1.5 hours. The reaction was purified by $C_{18}$ reverse phase automated HPLC (21 mgs, 67% yield, 100% pure, CO-AAW00024).

Synthesis of CO-AAW00025

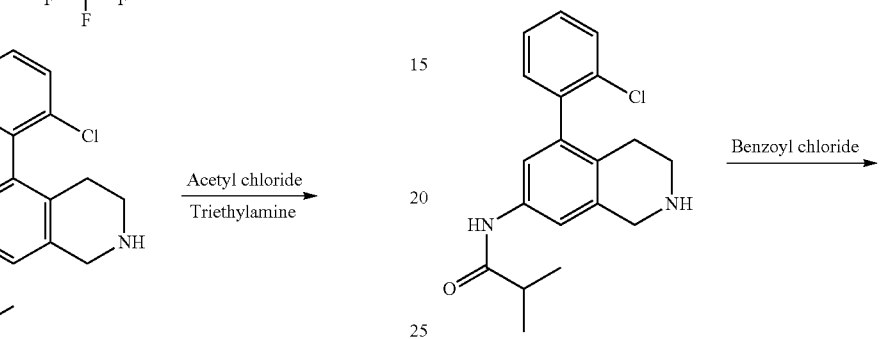

Synthesis of N-[5-(2-Chloro-phenyl)-1,2,3,4-tetrahydro-isoquinolin-7-yl]2-methylpropanamide (CO-AAW0003)

CO-AAW0001 (100 mgs, 0.24 mmoles) was dissolved in methanol (5 mls) followed by the addition of anhydrous potassium carbonate (50 mgs, 0.36 mmoles). The solution was stirred at room temperature for 2 hours. Silica thin layer chromatography in dichloromethane/methanol (95:5) showed reaction to be complete. The reaction was evaporated and the residue dissolved in ethylacetate (20 mls) and water (10 mls). The aqueous layer was re-extracted with ethylacetate (2×10 mls) and the combined organic phases washed with brine (10 mls), dried of magnesium sulphate, filtered and evaporated to produce a yellow oil (~80% pure, CO-AAW0003). This was used for the next reaction without further purification.

Synthesis of N-[2-Benzoyl-5-(2-chloro-phenyl)-1,2,3,4-tetrahydroisoquinolin-7-yl]2-methylpropanamide (CO-AAW00025)

N-[5-(2-Chloro-phenyl)-1,2,3,4-tetrahydro-isoquinolin-7-yl]2-methylpropanamide (39 mgs, 0.12 mmoles) was dissolved in dimethylacetamide (1 ml) followed by the addition of triethylamine (20 ul, 0.144 mmoles) and finally benzoyl chloride (16.7 ul, 0.144 mmoles). The reaction was stirred at room temperature for 1.5 hours and purified by $C_{18}$ reverse phase automated HPLC (14 mgs, 27% yield, 100% pure, CO-AAW0025).

General Reaction Scheme for Synthesis of 6-Benzyl Tetrahydropyridopyrimidines

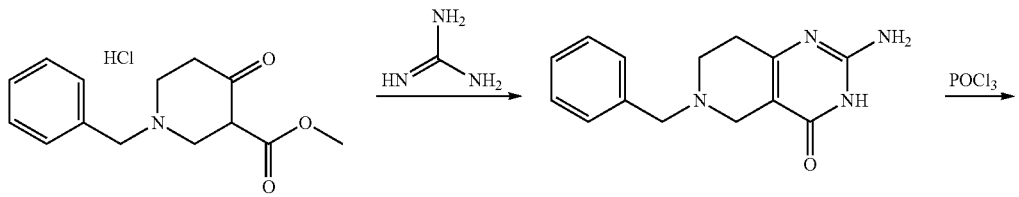

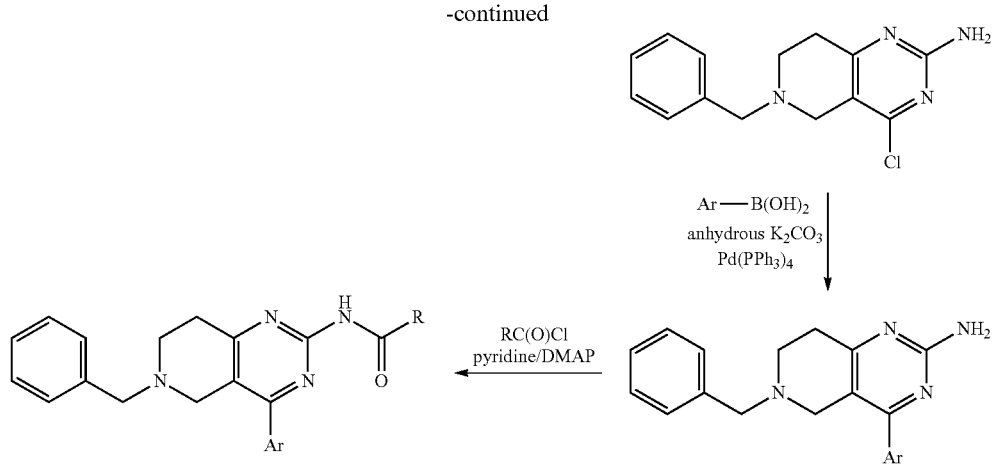

This reaction scheme will be further Illustrated by synthesis of CO-AAW00014, 16, 11, 12, 13, 15 and 32.

Synthesis of CO-AAW00014

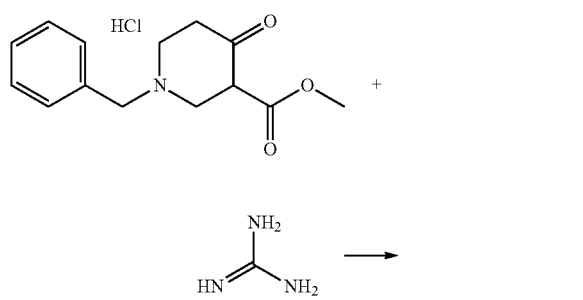

Synthesis of pentanoic acid [6-benzyl-4-(2-chloro-phenyl)-5,6,7,8-tetrahydro-pyrido[4,3-d]pyrimidin-2-yl]-amide Methyl-1-benzyl-4-oxo-3-piperidine carboxylate (5.68 g., 20 mmoles) and guanidine hydrochloride (2.0 g., 21 mmoles) were suspended and stirred in dry DMF (45 mls) before potassium carbonate (5.68 g., 41 mmoles) was added portionwise over 15 minutes. The reaction mixture was poured onto cold water (750 mls) to release a white/beige solid which was rapidly stirred for 30 minutes. The solid was filtered washed with water (100 mls) and dried in a vacuum desiccator. The product was then slurried in ether (150 mls), filtered and dried in vacuo overnight, to leave an off-white solid (4.46 g., 87% yield). Single spot by tlc (MeOH, Rf 0.66), LC-MS (retention 2.20 mins., mass 257 M+H).

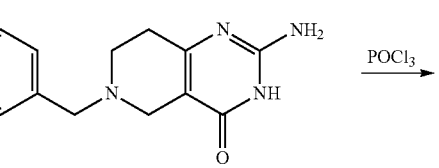

Synthesis of 6-benzyl-4-chloro-5,6,7,8-tetrahydro-pyrido[4,3-d]pyrimidin-2-ylamine Pentanoic acid [6-benzyl-4-(2-chloro-phenyl)-5,6,7,8-tetrahydro-pyrido[4,3-d]pyrimidin-2-yl]-amide (4.4 g, 17.2 mmoles) was added portionwise to stirred phosphorus oxychloride (40 mls). One drop of DMF was added to the reaction mixture and the yellow suspension was stirred and heated (110° C.) under nitrogen gas for 3.5 hours to generate a brown/yellow solution.

After cooling to room temperature the reaction mixture was poured onto ice/water (500 mls) with rapid stirring to generate an orange/yellow solution. The solution was cooled in ice and the pH adjusted to pH4 with concentrated ammonia. The solution was left overnight to produce a cloudy solution with pH9.0 and the solid was collected, washed with water (100 mls) and dried in a vacuum desiccator to yield an orange/yellow solid (2.7 g, 57% yield). LC-MS (retention 2.50 mins., mass 275 M+H).

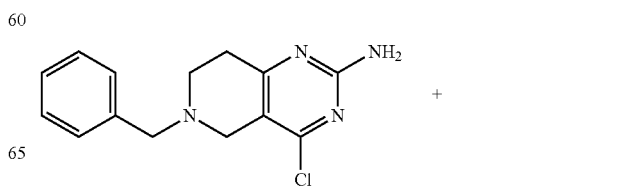

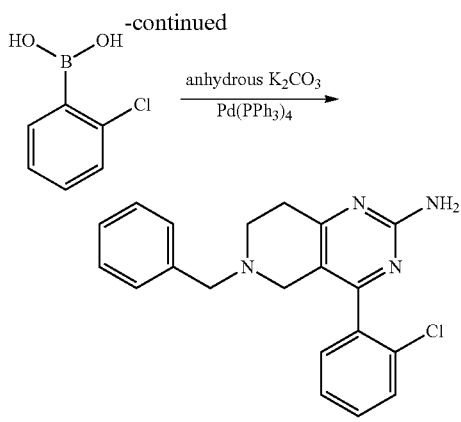

Synthesis of 6-benzyl-4-(2-chloro-phenyl)-5,6,7,8-tetrahydro-pyrido[4,3-d]pyrimidin-2-ylamine 6-benzyl-4-chloro-5,6,7,8-tetrahydro-pyrido[4,3-d]pyrimidin-2-ylamine (1.92 g., 7 mmoles) and 2-chlorophenylboronic acid (1.09 g., 7 mmoles) were mixed and stirred in a mixture of acetonitrile and water (50:50, 32 mls); anhydrous potassium carbonate (1.93 g., 14 mmoles) was then added to the stirred reaction mixture under nitrogen. $Pd(PPh_3)_4$ (0.2 g.) was then added to the reaction mixture which was stirred and heated at 95° C. for 3 hours also under nitrogen. The reaction mixture was then allowed to cool to room temperature and a beige solid formed. This suspension was quenched with water (150 mls) and the solid filtered and washed with water (100 mls) dried in a vacuum desiccator. The product was then eluted through a 'silica plug' in ethyl acetate, after evaporation the solid was slurried in ether to give, after filtering and drying a white solid (1.5 g., 61.2% yield). LC-MS (retention 2.65 mins, mass 351 M+H).

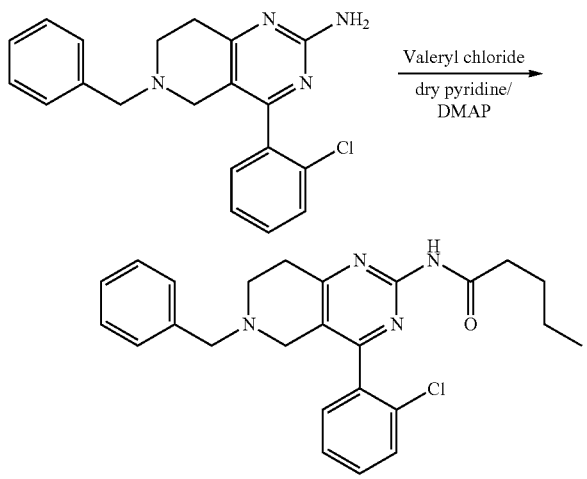

Synthesis of pentanoic acid [6-benzyl-4-(2-chloro-phenyl)-5,6,7,8-[4,3-d]pyrimidin-2-yl]-amide (CO-AAW00014)

6-benzyl-4-(2-chloro-phenyl)-5,6,7,8-tetrahydro-pyrido[4,3-d]pyrimidin-2-ylamine (4.26 g., 12.15 mmoles) was dissolved in dry pyridine (50 mls) before the addition of valeryl chloride (1.73 mls., 1.2 equivalents) dropwise over 5 minutes. To this reaction mixture was then added dimethyl amino pyridine (100 mgs) and the mixture was stirred and heated to 50° C. overnight under nitrogen. The pyridine was then removed in 'vacuo' and the dark brown oil partitioned between ethyl acetate (200 mls) and water (200 mls). The aqueous layer was removed and further extracted with ethyl acetate (200 mls), the combined ethyl acetate extracts were then washed with sodium bicarbonate solution (100 mls) then water (50 mls) and finally brine (100 mls). The resulting ethyl acetate extract was then dried by the addition of magnesium sulphate, filtered and concentrated to leave a brown oil (6.0 g.) This oil was subjected to silica gel chromatography (ethyl acetate/hexane 1:1). Fractions 9-15 gave pure product (97%, 3.05 g., 58% yield). LC-MS (retention 3.00 mins., mass 435.2 M+H).

Synthesis of CO-AAW00016

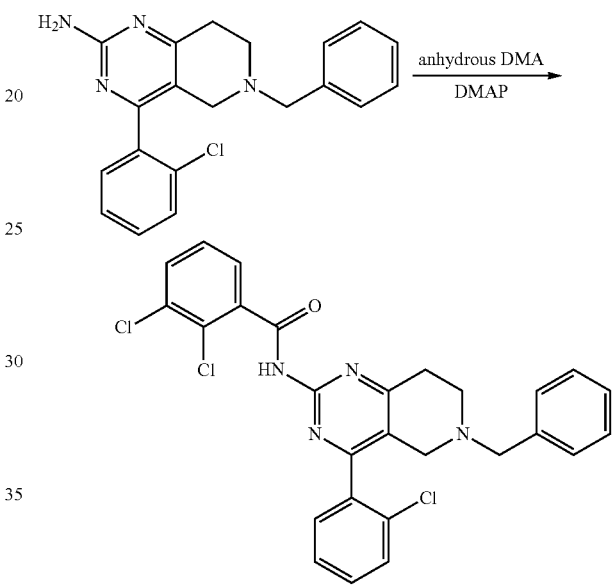

Synthesis of N-[6-benzyl-4-(2-chlorophenyl)-5H,6H,7H,8H-pyrido[4,3-d]pyrimidin-2-yl]-2,3-dichlorobenzamide (CO-AAW00016)

6-benzyl-4-(2-chlorophenyl)-5H,6H,7H,8H-pyrido[4,3-d]pyrimidin-2-yl]-amine (0.070 g, 0.2 mmoles) was dissolved in anhydrous Dimethylacetamide (2 mls) and N,N-dimethylamino pyridine (0.03 mg, 0.24 mmoles) added followed by 2,3-dichlorobenzoyl chloride (0.1581 g, 0.72 mmoles) and the reaction heated (40° C.) and left for 72 hours. The reaction was filtered and purified by automated C18 HPLC (0.0119 g, 100% pure, CO-AAW00016).

Synthesis of CO-AAW00011

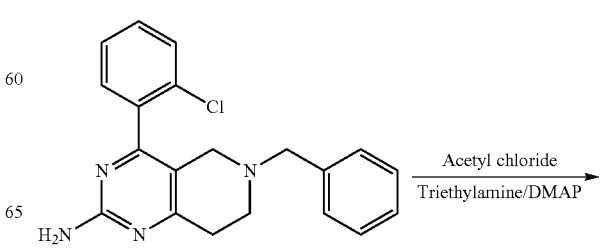

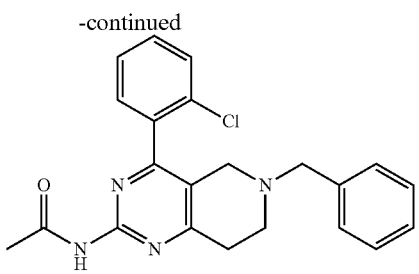

Synthesis of N-[6-Benzyl-4-(2-chloro-phenyl)-5,6,7,8-tetrahydro-pyrido[4,3-d]pyrimidin-2-yl]-acetamide (CO-AAW00011)

6-benzyl-4-(2-chlorophenyl)-5H,6H,7H,8H-pyrido[4,3-d]pyrimidin-2-yl]-amine (70 mgs, 0.2 mmoles) was dissolved in anhydrous dimethylacetamide (1 ml) to which was added acetyl chloride (34 ul, 0.48 mmoles), triethylamine (34 ul, 0.24 mmoles) and dimethylaminopyridine (60 mgs, 0.48 mmoles) and the reaction stirred and heated (40° C.) for 48 hours. The reaction was purified by $C_{18}$ reverse phase automated HPLC (9.1 mgs, 11.5% yield, 100% pure, CO-AAW00011).

Synthesis of CO-AAW00012

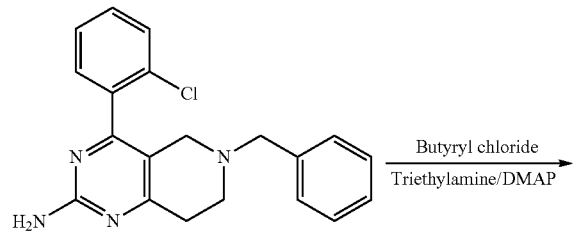

Synthesis of N-[6-Benzyl-4-(2-chloro-phenyl)-5,6,7,8-tetrahydro-pyrido[4,3-d]pyrimidin-2-yl]-butylamide (CO-AAW00012)

6-benzyl-4-(2-chlorophenyl)-5H,6H,7H,8H-pyrido[4,3-d]pyrimidin-2-yl]-amine (70 mgs, 0.2 mmoles) was dissolved in anhydrous dimethylacetamide (1 ml) to which was added butyryl chloride (50.6 ul, 0.48 mmoles), triethylamine (34 ul, 0.24 mmoles) and dimethylaminopyridine (60 mgs, 0.48 mmoles) and the reaction stirred and heated (40° C.) for 48 hours. The reaction was purified by $C_{18}$ reverse phase automated HPLC (16.1 mgs, 19% yield, 100% pure, CO-AAW00012).

Synthesis of CO-AAW00013

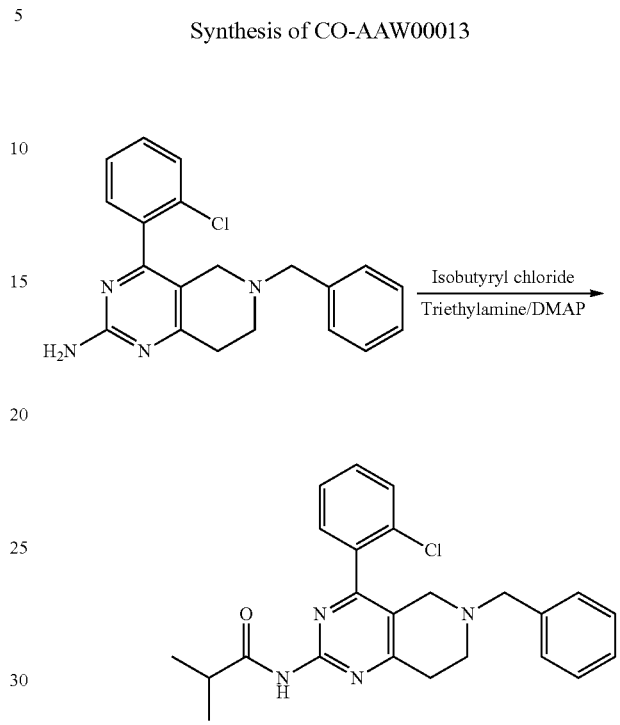

Synthesis of N-[6-Benzyl-4-(2-chloro-phenyl)-5,6,7,8-tetrahydro-pyrido[4,3-d]pyrimidin-2-yl]2-methyl-propanamide (CO-AAW00013)

6-benzyl-4-(2-chlorophenyl)-5H,6H,7H,8H-pyrido[4,3-d]pyrimidin-2-yl]-amine (70 mgs, 0.2 mmoles) was dissolved in anhydrous dimethylacetamide (1 ml) to which was added isobutyryl chloride (50.6 ul, 0.48 mmoles), triethylamine (34 ul, 0.24 mmoles) and dimethylaminopyridine (60 mgs, 0.48 mmoles) and the reaction stirred and heated (40° C.) for 48 hours. The reaction was purified by $C_{18}$ reverse phase automated HPLC (14.4 mgs, 17.1% yield, 100% pure, CO-AAW00013).

Synthesis of CO-AAW00015

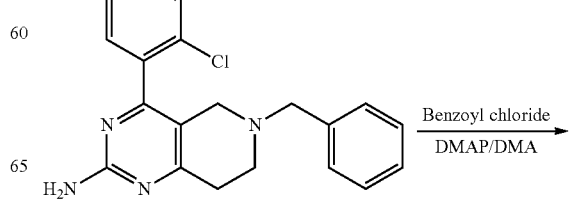

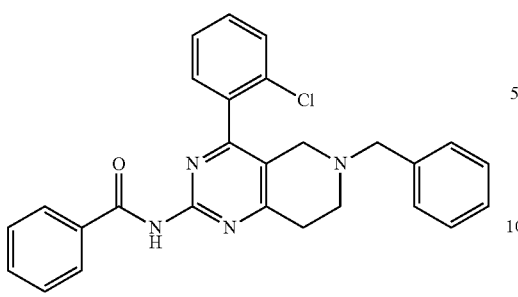

Synthesis of N-[6-Benzyl-4-(2-chloro-phenyl)-5,6,7,8-tetrahydro-pyrido[4,3-d]pyrimidin-2-yl]-benzamide (CO-AAW00014)

6-benzyl-4-(2-chlorophenyl)-5H,6H,7H,8H-pyrido[4,3-d]pyrimidin-2-yl]-amine (70 mgs, 0.2 mmoles) was dissolved in anhydrous dimethylacetamide (2 ml) to which was added benzoyl chloride (84 ul, 0.72 mmoles) and dimethylaminopyridine (30 mgs, 0.24 mmoles) and the reaction stirred and heated (40° C.) for 48 hours. The reaction was purified by $C_{18}$ reverse phase automated HPLC (21 mgs, 23.1% yield, 90% pure, CO-AAW00014).

Synthesis of CO-AAW00032

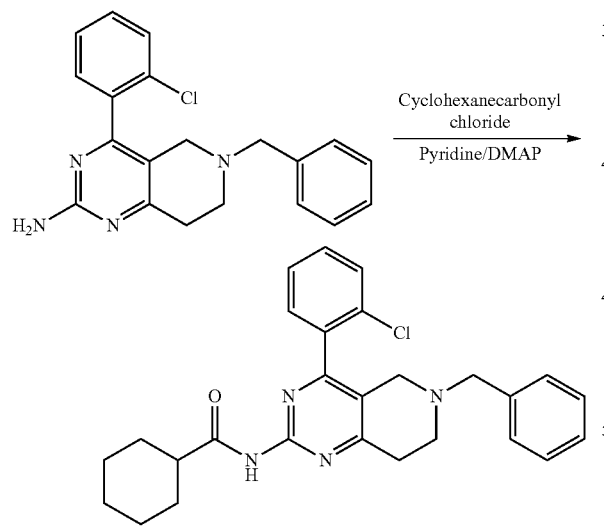

Synthesis of cyclohexanecarboxylic acid [6-benzyl-4-(2-chlorophenyl)-5,6,7,8-tetrahydro-pyridin[4,3-d]pyrimidin-2-yl]-amide (CO-AAW00032)

6-benzyl-4-(2-chlorophenyl)-5H,6H,7H,8H-pyrido[4,3-d]pyrimidin-2-yl]-amine (71 mgs, 0.2 mmoles) was dissolved in pyridine (2 mls) followed by the addition of cyclohexanecarbonyl chloride (128 ul, 0.96 mmoles) and DMAP (60 mgs, 0.48 mmoles). The reaction was then flushed with nitrogen and stirred with heating (50° C.) overnight. The product was purified by semi-preparative $C_{18}$ HPLC (44.8 mgs, 48% yield, 100% pure, CO-AAW00032).

Synthesis of CO-AAW00033

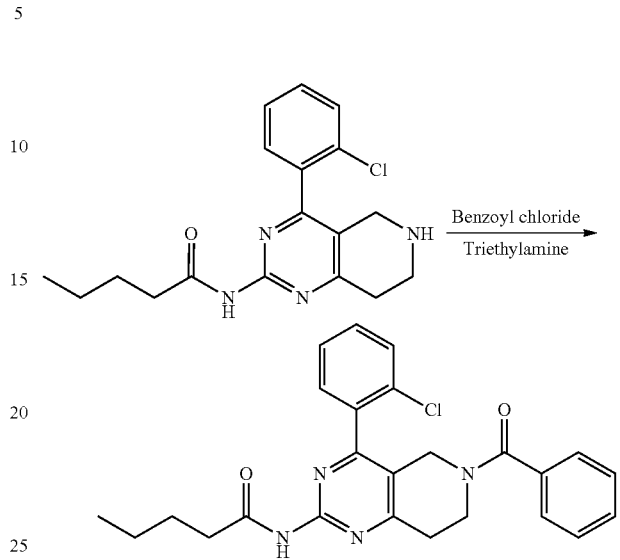

Synthesis of pentanoic acid [6-benzoyl-4-(2-chlorophenyl)-5,6,7,8-tetrahydro-pyrido[4,3-d]pyrimidin-2-yl]-amide (CO-AAW00033)

Pentanoic acid [4-(2-chlorophenyl)-5,6,7,8-tetrahydropyrido[4,3-d]pyrimidin-2-yl]amide (~50% pure, 150 mgs) was suspended in anhydrous dimethylacetamide (2 mls) followed by the addition of benzoyl chloride (75 ul, 0.65 mmoles) and then triethylamine (90 ul, 0.65 mmoles). The reaction was flushed with nitrogen and stirred at room temperature overnight. The reaction was incomplete so further aliquots of benzoyl chloride (75 ul, 0.65 mmoles) and then triethylamine (90 ul, 0.65 mmoles) were added. The reaction, after a further three hours was purified by semi-preparative $C_{18}$ HPLC (31 mgs, 16% yield, 100% pure, CO-AAW00033).

The starting material to the synthesis of CO-AAW00033 shown above (pentanoic acid[4-(2-chlorophenyl)-5,6,7,8-tetrahydro-pyrido[4,3-d]pyrimdin-2-yl]amide) is prepared by treatment of an N-substituted compound, such as CO-AAW000012, with $K_2CO_3$/MeOH, in line with step 4a of the general reaction scheme shown above for the synthesis of tetrahydroisoquinolines. It will be appreciated that this reaction scheme can be varied to produce other tetrahydroisoquinolines for example by utilising alternative N-substituted compounds and/or replacing benzoyl chloride with alternative chloride compounds.

General Reaction Scheme for the Synthesis of Aryl Isoquinoline Carboxamides

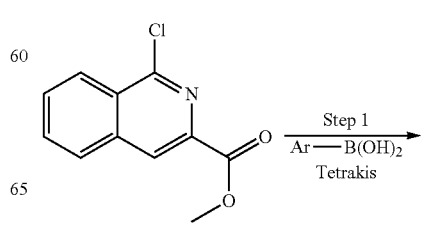

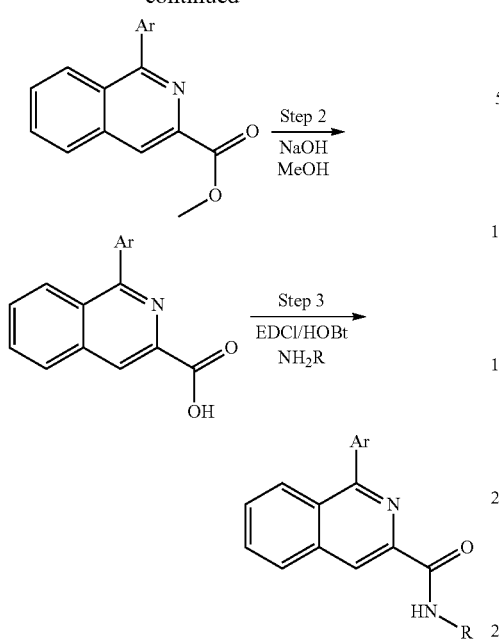

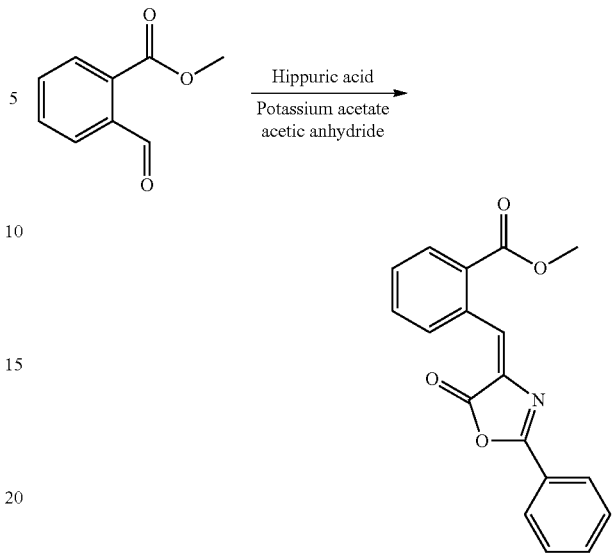

Synthesis of 2-carboxymethylbenzaldehyde hippuric acid adduct

2-Carboxymethylbenzaldehyde (4.9 g, and 30 mmoles) with hippuric acid (5.9 g, 33 moles) and potassium acetate (2.94 g, 30 mmoles) were added to acetic anhydride (14.2 mls, 150 mmoles) and the reaction heated (100° C.) for 4 hours. To the cooled reaction was added water (100 mls) and stirred overnight. The resulting solid was collected by filtration and washed with water and dried (7.6 g, 83% yield).

The starting material in the above general reaction scheme, methyl 4-chloroisoquinoline-2-carboxylate, can be prepared by the route set out below. Following this, the reaction scheme will be further illustrated by synthesis of the reference example CO-AAW0005.

Synthesis of methyl 4-chloroisoquinoline-2-carboxylate

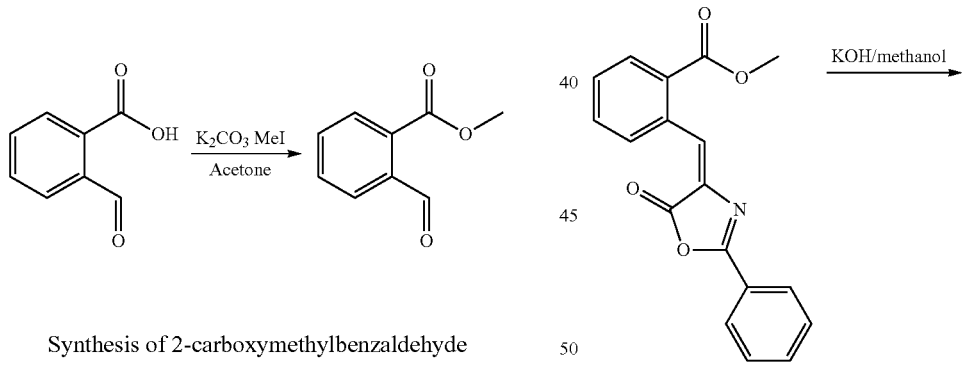

Synthesis of 2-carboxymethylbenzaldehyde

2-Carboxybenzaldehyde (4.53 g, 30 mmoles) was dissolved in acetone (100 mls) and anhydrous potassium carbonate (4.14 g, 30 mmoles) was added. After stirring methyl iodide (5.6 mls, 90 mmoles) was added and the reaction was heated (56° C.) for 30 minutes. The reaction became very thick so further acetone was added (50 mls) and stirring continued at room temperature for a further 72 hours. The reaction mixture was filtered through Celite and then evaporated to leave a viscous oil. The oil was then partitioned between water (30 ml) and ethyl acetate (30 ml). The aqueous layer was washed with further ethyl acetate (2×30 mls) and all the ethyl acetate extracts combined and washed with brine (30 mls) and then water (30 mls) dried over anhydrous magnesium sulphate and evaporated to leave a clear light yellow oil (4.9 g, 100% yield).

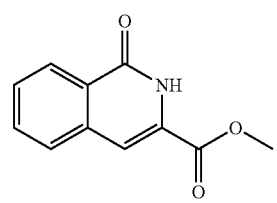

Synthesis of methyl 1-oxo-1,2-dihydroisoquinoline-3-carboxylate

The 2-carboxymethylbenzaldehyde hippuric acid adduct from above (1.0 g, 3.3 mmoles) was dissolved in methanol (20 mls) and solid potassium hydroxide (0.37 g, 6.6 mmoles) was added. The clear solution was heated (65° C.) for 1 hour.

The reaction was evaporated and the solid residue partitioned between water (25 mls) and ethyl acetate (25 mls). The aqueous layer was further extracted with ethyl acetate (2×10 mls) and the combined ethyl acetate extracts washed with brine (10 mls) water (10 mls). After drying over magnesium sulphate the solution was evaporated to leave a yellow solid (0.68 g, 99% yield).

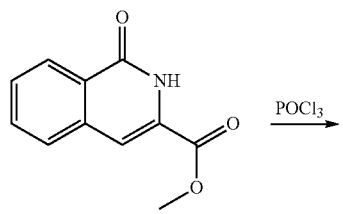

Synthesis of methyl 4-chloroisoquinoline-2-carboxylate

Methyl 1-oxo-1,2-dihydroisoquinoline-3-carboxylate (0.68 g, 3.3 mmoles) was dissolved in excess phosphorus oxy chloride (5 mls) and the clear solution heated (95° C.) for 3 hours and overnight at room temperature. The reaction was diluted with toluene (10 mls) and azeotroped twice. The residual oil was diluted with dichloromethane (10 mls) and quenched with ice cooled water (50 mls). Further dichloromethane was added (15 mls) and the layers separated. The aqueous layer was extracted with dichloromethane (10 mls) and the dichloromethane phases combined and washed with saturated sodium bicarbonate (10 mls), water (10 mls) and brine (10 mls). After drying over magnesium sulphate the solution was filtered and concentrated to give an off white solid. (0.47 g, 64% yield).

Specific Example of Step 1

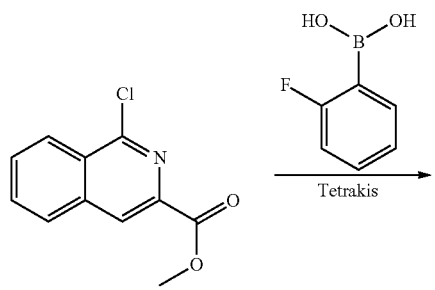

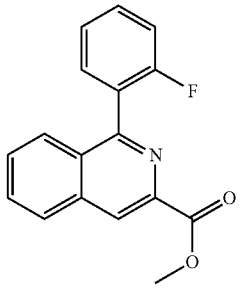

Synthesis of methyl 1-(2-fluorophenyl) isoquinoline-3-carboxylate

Methyl 4-chloroisoquinoline-2-carboxylate (0.221 g, 1 mmole) was dissolved in toluene (10 mls) and 2-fluorophenylboronic acid (0.280 mgs, 2 mmoles), anhydrous potassium carbonate (0.276 g, 2 mmoles) and tetrakis (0.060 mgs) was added and the vessel flushed with nitrogen. The reaction was heated (95° C.) overnight and after cooling the reaction was filtered through silica the filtrate was then washed with saturated sodium bicarbonate solution (10 mls), water (10 mls) and then brine (10 mls). After drying over magnesium sulphate and evaporating an off white solid (140 mgs, 50% yield, 95% pure was left.

Specific Example of Step 2—Hydrolysis of Isoquinoline Esters

Synthesis of 1-(2-fluorophenyl) isoquinoline-3-carboxylic acid

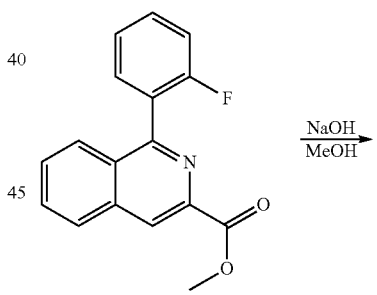

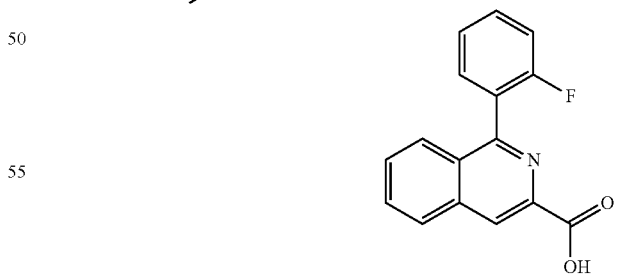

Methyl 1-(2-fluorophenyl)isoquinoline-3-carboxylate (0.096 g, 0.34 mmoles) was dissolved in methanol (5 mls) followed by sodium hydroxide (1M, 0.51 mls, 0.51 mmoles) and the reaction heated (40° C.) overnight. The solution was then evaporated and the residue diluted with water (10 mls), and ethyl acetate (10 mls). This mixture was then acidified hydrochloric acid (1M HCl) to ~pH 5.0 and the layers separated. The aqueous layer was further extracted with ethyl acetate (2×10 mls) and the organic layers combined and washed with water (10 mls) and brine (10 mls). The organic solution was evaporated to leave a white residue (0.091 mgs, 100% yield, 90% pure).

Specific Example of Step 3—Synthesis of CO-AAW0005

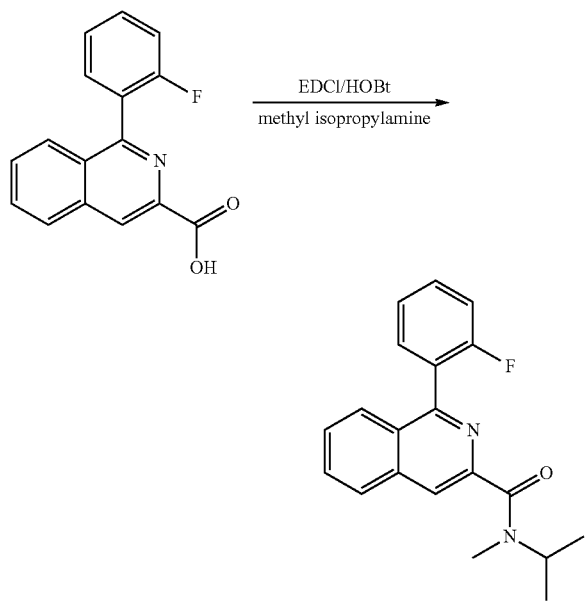

Synthesis of 1-(2-fluorophenyl)-N-methyl-N(propan-2-yl) isoquinoline carboxamide (CO-AAW0005)

1-(2-fluorophenyl)isoquinoline-3-carboxylic acid (0.910 mgs, 0.34 mmoles) was dissolved in dimethylacetamide (2 mls) to which was added methyl isopropylamine (0.039 mls, 0.37 mmoles), 1-ethyl-3-(3-dimethylaminopropyl)carbodiimide (EDCI, 0.071 g, 0.37 mmoles), hydroxyl benzotriazole (HOBt, 0.046 g, 0.34 mmoles) and N,N-diisopropylethylamine (0.056 mls, 0.34 mmoles). The reaction was stirred at room temperature overnight and after evaporation the product was purified by automated C18 HPLC (52.6 mgs, 48% yield, 100% pure, CO-AAW0005).

The above reaction step can be varied to produce, for example, a compound having a —C(O)NHalkyl substituent rather than a —C(O)N(Me)(propanyl) substituent by replacing the methyl isopropylamine with the appropriate amine, $NH_2$alkyl.

Treatment of DoHH2 (Lymphoma) Cell Line

Measurement of Mitochondrial Membrane Potential depolarisation and mitochondrial permeability transition (MPT). Cells were incubated for 20 minutes at 37° C. in the dark with the cationic lipophillic (amphipathic) probe 3,3'-dihexyloxacarbocyanine iodide, $DiOC_6(3)$ (80 nM), then counter stained for 10 minutes with propidium iodide (20 μg/ml). $DiOC_6(3)$ is sequestered within the mitochondrial matrix due to the inner membrane potential ($\Delta\psi_m$), according to the Nernst equation, dissipation leading to a reduction in mitochondrial retention and decreased cellular $DiOC_6(3)$ fluorescence. Collapse of $\Delta\psi_m$ was prevented by incubating cells for 30 minutes with 50 μM bongkrekic acid. Events with increased propidium iodide fluorescence were subtracted, by gating, from the $DiOC_6(3)$ histograms to eliminate dead cells, with loss of plasma membrane integrity. Dose-response curves used the calculated proportion of $DiOC_6(3)_{low}$ cells as the dependent variable on the ordinate. To measure MPT directly, cells were incubated with 1 μM calcein AM for 30 minutes, followed by 1 mM calcium cobalt. Cobalt quenches calcein fluorescence, but cannot traverse an intact inner mitochondrial membrane to enter the mitochondrial matrix, to which calcein equilibrates. Opening of the PTPC allows cobalt to enter, reducing calcein fluorescence.

The Lymphoma cell line (DoHH2) was treated with PK11195 and various compounds of the invention at doses of 10 and 50 μmol concentrations. Levels of cell viability and apoptosis were measured by DiOC6 flow evaluation. DiOC6 is a fluorescent dye which acts as a surrogate marker of mitochondrial depolarisation. Uptake of DiOC6 and consequent fluorescence is a measure of opening of the permeability transition pore complex (PTPC). FIG. 1 shows results of various compounds tested, all of which induced a level of apoptosis. CO-AAW0001 (AAW-001), CO-AAW00014 (AAW-0014), CO-AAW00017 (AAW-0017) and CO-AAW00022 (9MK-328) were shown to be substantially superior to PK11195 at a concentration of 50 μM in inducing apoptosis (by a factor of at least 4-fold) in the malignant cell line.

Treatment of HL60 Leukaemia Cell Line

The Leukemia cell line (HL60) was incubated with PK11195 or various compounds of the invention. As described above for the DoHH2 cell line, levels of cell viability and apoptosis were measure by DiOC6 flow evaluation. At a concentration of 50 μM, CO-AAW0001 (AAW-001), CO-AAW00014 (AAW-0014), CO-AAW00017 (AAW-0017) and CO-AAW00022 (9MK-328) were shown to be substantially superior to PK11195 at a concentration of 50 μM in inducing apoptosis (by a factor of at least 3-fold) in the HL60 cell line.

Superoxide Purging with MnTBAP

Measurement and inhibition of Hydrogen Peroxide and $O^{2-\cdot}$ Generation $O^{2-\cdot}$ was detected by incubating cells for 15 minutes in 5 μM dihydroethidium, which is oxidized to ethidium. To test the effect of $O^{2-\cdot}$ dismutase inhibitor on $O^{2-\cdot}$ generation, cells were treated with 100 μM MnTBAP for 45 minutes. Hydrogen peroxide was detected by loading cells for 30 minutes with 5 μM CM-$H_2$DCFDA, and its formation inhibited by preincubation with 500 U/ml catalase for 30 minutes. Dose-response curves for CM-$H_2$DCFDA used the calculated proportion of CM-$H_2$DCFDA$_{high}$ cells as the dependent variable.

DoHH2 cells were exposed to AAW-001, AAW-0014 and PK11195 in the presence and absence of the mitochondrial reactive oxygen species (ROS) scavenger MnTBAP.

Figure 2:
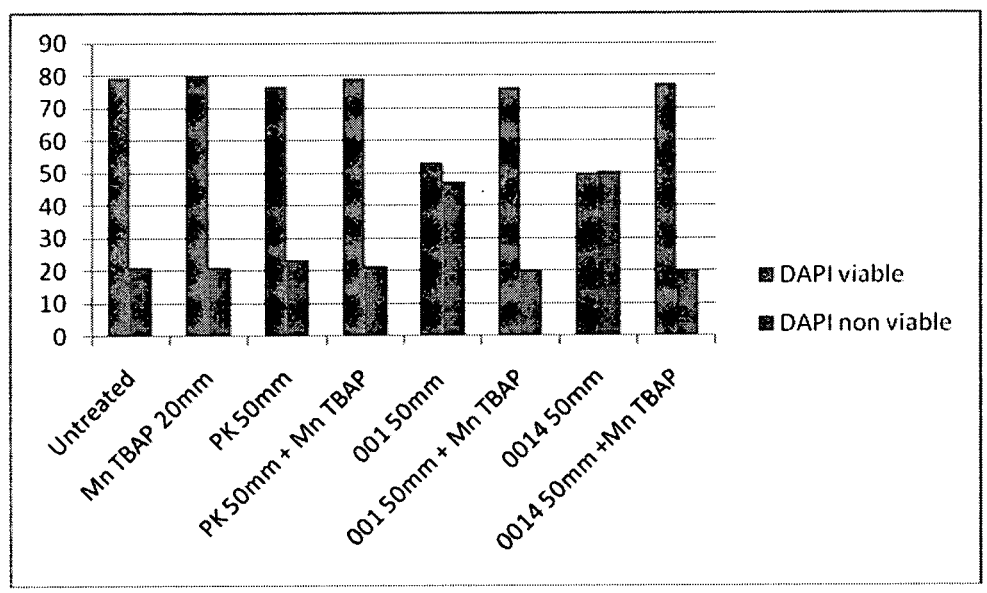
FIG. 2 shows the results of superoxide purging with MnTBAP at 20 µl on cell viability and apoptosis of two compounds of the invention compared to PK11195 using the DoHH2 (lymphoma) cell line. With both compounds, the ability to induce apoptosis was inhibited by MnTBAP, suggesting a pivotal role for superoxide generation. For each entry in FIG. 2, DAPI viable is on the left and DAPI non viable is on the right.
Figure 3:
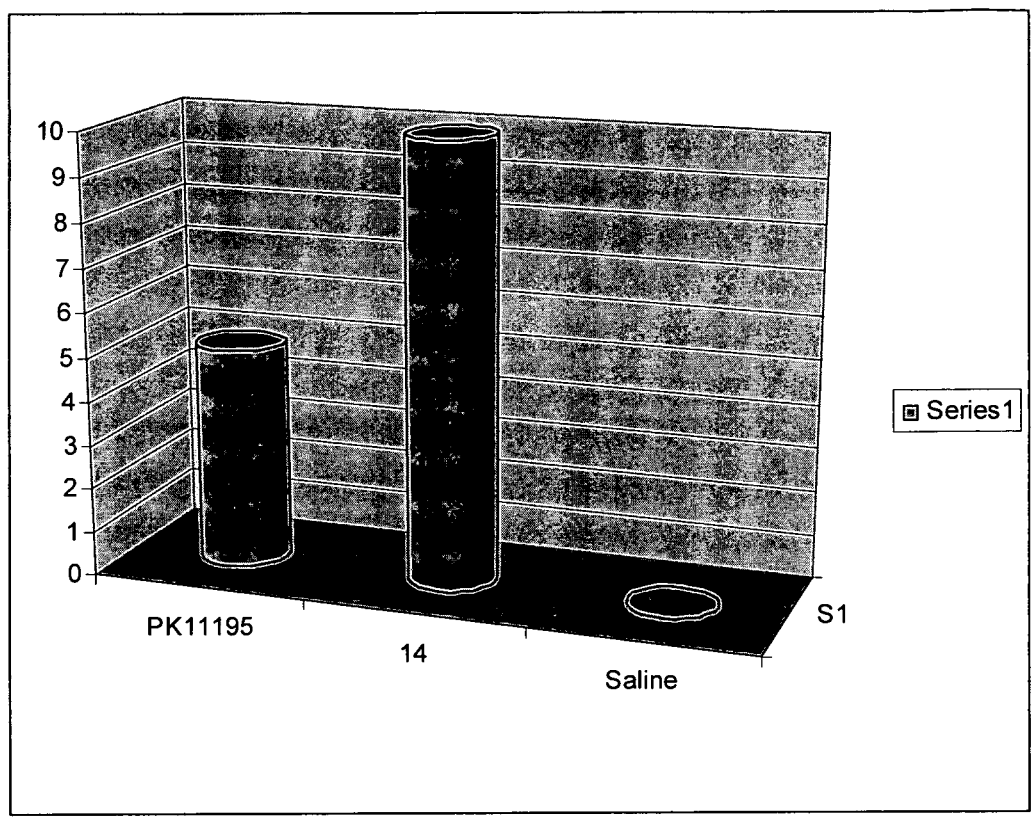
FIG. 3 shows 10 week % survival rates for mature DoHH2 Xenograft NOD/SCID mice treated 2 weeks post inoculation with the human B cell lymphoma cell line DoHH2, where the mice were dosed with AAW-0014, PK11195 or saline.

For both CO-AAW0001 and CO-AAW00014, the ability to induce apoptosis was inhibited by MnTBAP suggesting a pivotal role for superoxide generation in the action of these agents. These results are shown in FIG. 2.

Additional Apoptosis and Cell Viability Data

The following tables set out % viability and % apoptosis results seen for treatment of DoHH2 cells with certain compounds of the invention at a dosage of 50 μM, in comparison with untreated cells. The assay procedure used was as described above in respect of "Treatment of DoHH 2 (Lymphoma) Cell Line".

TABLE 1

Percentage Cell Viability

| | | Compound (CO-AAW000...) | | | | | | | | | | | |
|---|---|---|---|---|---|---|---|---|---|---|---|---|---|
| Repeat | Untreated | 1 | 7 | 8 | 9 | 14 | 16 | 17 | 18 | 30 | 20 | 22 | 25 |
| 1 | 81.6 | 48.5 | 63.9 | 54.1 | 48.8 | | | | | | | | |
| 2 | 92.2 | 68.4 | 88.2 | 81.7 | 90.5 | | | | | | 72.7 | | |
| 3 | 91.8 | 68.4 | | | | | | | | | | 37.4 | 56.3 |
| 4 | 93.3 | 65.4 | | | | | | | | | 78.7 | 19.4 | 78.8 |
| 5 | 82.3 | 73.8 | | | | 68.8 | 78.5 | 74.2 | 84.8 | | | | |
| 6 | 92.3 | 67.7 | | | | 42.3 | 76.5 | 68.4 | 79.2 | | | | |
| 7 | 89.0 | 47.9 | | | | 39.4 | | | | 64.3 | | | |
| 8 | 87.0 | 62.5 | | | | 65.8 | | | | | | | |
| 9 | 89.4 | 48.0 | | | | 51.8 | | | | | | | |
| 10 | 80.3 | 52.8 | | | | 54.3 | | | | | | | |
| 11 | 79.2 | 52.9 | | | | 49.6 | | | | | | | |
| Averages | 87.1 | 59.7 | 76.1 | 67.9 | 69.9 | 53.1 | 77.5 | 71.3 | 82.0 | 64.3 | 75.7 | 28.4 | 67.6 |

TABLE 2

Percentage Cell Apoptosis

| | | Compound (CO-AAW000...) | | | | | | | | | | | |
|---|---|---|---|---|---|---|---|---|---|---|---|---|---|
| Repeat | Untreated | 1 | 7 | 8 | 9 | 14 | 16 | 17 | 18 | 30 | 20 | 22 | 25 |
| 1 | 11.7 | 60.7 | 35.1 | 48.8 | 52.5 | | | | | | | | |
| 2 | 10.6 | 56.8 | 17.0 | 29.5 | 12.3 | | | | | | | | |
| 3 | 5.8 | 25.1 | | | | | | | | | 17.1 | 62.9 | 19.7 |
| 4 | 5.0 | 34.2 | | | | | | | | | 17.4 | 67.8 | 11.1 |
| 5 | 20.7 | 39.1 | | | | 50.0 | 33.4 | 43.0 | 25.6 | | | | |
| 6 | 8.2 | 49.2 | | | | 74.1 | 33.6 | 55.3 | 22.5 | | | | |
| 7 | 17.9 | 80.0 | | | | 81.9 | | | | 61.2 | | | |
| 8 | 19.4 | 50.9 | | | | 56.7 | | | | | | | |
| 9 | 12.3 | 64.9 | | | | 69.2 | | | | | | | |
| 10 | 23.7 | 58.0 | | | | 58.9 | | | | | | | |
| 11 | 20.4 | 62.1 | | | | 67.4 | | | | | | | |
| Averages | 14.2 | 52.8 | 26.1 | 39.2 | 32.4 | 65.5 | 33.5 | 49.2 | 24.1 | 61.2 | 17.3 | 65.4 | 15.4 |

Testing in DoHH2 Xenograft Mice

NOD/SCID mice xenografted with the human lymphoma DoHH2 cell line were treated two weeks post inoculation with the human B cell lymphoma cell line DoHH2. There were three cohorts of ten mice. For two cohorts, treatment consisted of 50 microgram intraperitoneal (IP) doses twice weekly for three weeks of PK11195 or AAW-0014, respectively. The third cohort was treated with 200 microlitres of saline twice weekly over a 3 week period. The mice were then observed for up to six weeks. All of the saline treated mice were dead due to disease at 10 weeks. Five of the ten PK11195 mice were alive at 10 weeks but on culling showed moderate levels of disease on splenic assessment. All of the AAW-0014 treated mice were alive at 10 weeks showing less than 20% splenic involvement, including 2 mice with no detectable disease. No major drug related toxicities were observed.

It will be appreciated to a skilled person reading this disclosure that various changes in form and detail can be made without departing from the true scope of the invention and such changes are encompassed by the invention.

The invention claimed is:

1. A compound of Formula (I) or a pharmaceutically acceptable salt thereof

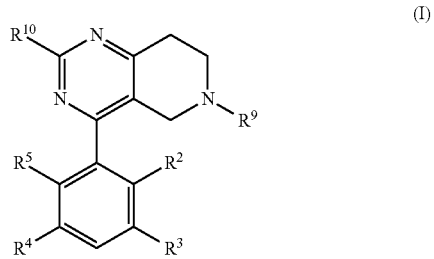

(I)

wherein $R^2$, $R^3$, $R^4$ and $R^5$ are each independently hydrogen, lower alkyl, $-NH_2$, $-NO_2$, $-OH$, $-CN$ or halogen, provided that at least one of $R^2$ and $R^5$ is halogen;

$R^9$ is —$R^{11}$ or —C(O)$R^{11}$, wherein $R^{11}$ is optionally substituted aliphatic, haloalkyl, aryl, heteroaryl, alkylaryl, alkylheteroaryl, carbocycle or heterocycle; and $R^{10}$ is —$NO_2$, —$NH_2$, —NHC(O)$R^{12}$, —C(O)NH$R^{12}$ or —NHS(O)$_2R^{12}$, wherein $R^{12}$ is optionally substituted aliphatic, alkylaryl, alkylheteroaryl, aryl, heteroaryl, carbocycle or heterocycle.

2. The compound of claim 1, wherein $R^2$, $R^3$, $R^4$ and $R^5$ are each independently hydrogen or halogen, provided that at least one of $R^2$ and $R^5$ is halogen.

3. The compound of claim 2, wherein $R^3$ and $R^4$ are hydrogen.

4. The compound of claim 3, wherein one of $R^2$ and $R^5$ is halogen and the other of $R^2$ and $R^5$ is hydrogen, or both of $R^2$ and $R^5$ are halogen.

5. The compound of claim 1 wherein $R^9$ is —$R^{11}$ and $R^{11}$ is alkylaryl or alkylheteroaryl or $R^9$ is —C(O)$R^{11}$, wherein $R^{11}$ is alkyl, haloalkyl or substituted or unsubstituted aryl.

6. The compound of claim 1, wherein $R^{10}$ is —NHC(O)$R^{12}$.

7. The compound of claim 1, wherein the compound is selected from:

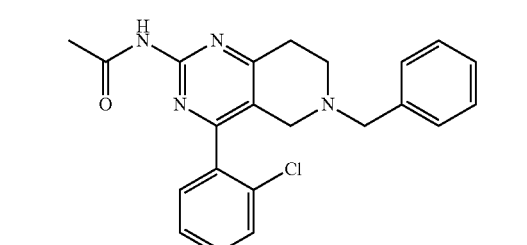

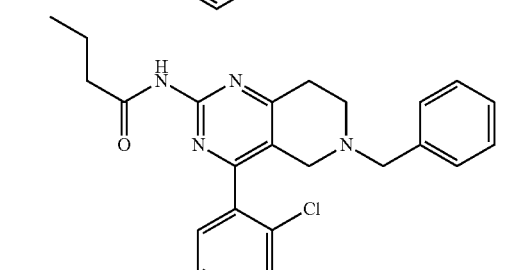

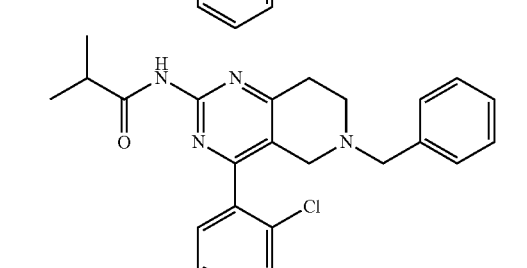

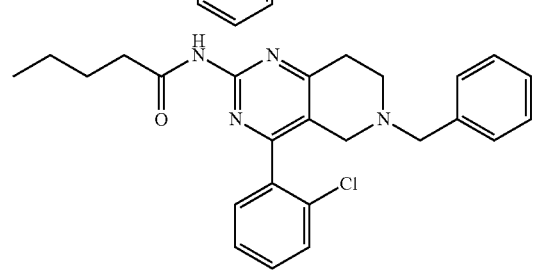

-continued

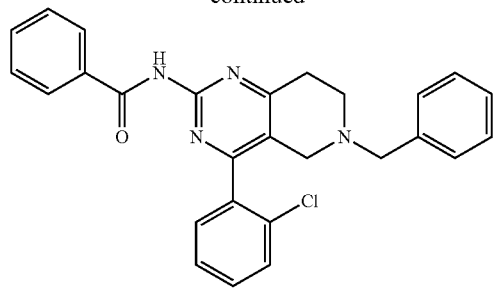

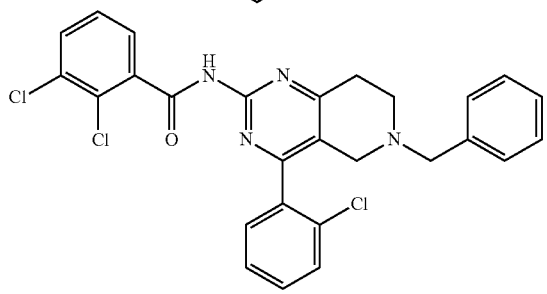

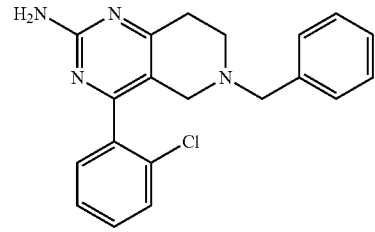 [SMILES: Nc1nc2c(c(-c3ccccc3Cl)n1)CN(Cc1ccccc1)CC2]

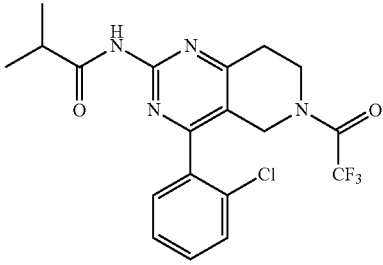 [SMILES: CC(C)C(=O)Nc1nc2c(c(-c3ccccc3Cl)n1)CN(C(=O)C(F)(F)F)CC2]

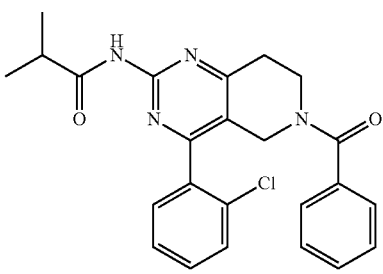

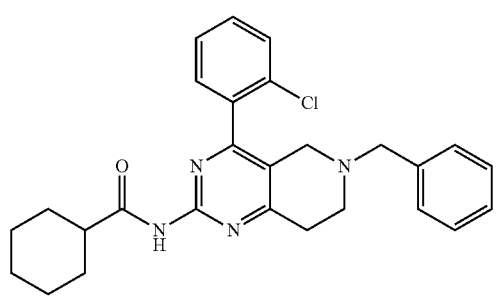

-continued

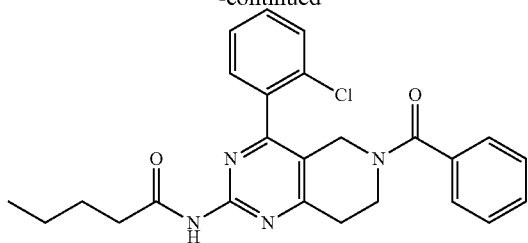

or a pharmaceutically acceptable salt thereof.

8. A compound of Formula (II), or a pharmaceutically acceptable salt thereof,

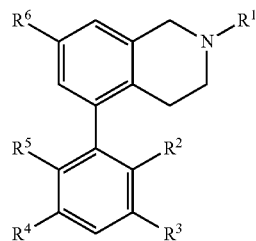

(II)

wherein

R$^2$, R$^3$, R$^4$ and R$^5$ are each independently hydrogen, halogen, lower alkyl, —NH$_2$, —NO$_2$, —OH or —CN, provided that at least one of R$^2$ and R$^5$ is halogen;

R$^1$ is —R$^7$, or —C(O)R$^7$, wherein R$^7$ is optionally substituted aliphatic, haloalkyl, aryl, heteroaryl, alkylaryl, alkylheteroaryl, carbocycle or heterocycle; and R$^6$ is hydrogen, —NO$_2$, —NH$_2$, —NHC(O)R$^8$, —C(O)NHR$^8$ or —NHS(O)$_2$R$^8$, wherein R$^8$ is optionally substituted aliphatic, alkylaryl, alkylheteroaryl, aryl, heteroaryl, carbocycle or heterocycle.

9. The compound of claim 8, wherein R$^2$, R$^3$, R$^4$ and R$^5$ are each independently hydrogen or halogen, provided that at least one of R$^2$ and R$^5$ is halogen.

10. The compound of claim 9, wherein R$^3$ and R$^4$ are hydrogen.

11. The compound of claim 10, wherein one of R$^2$ and R$^5$ is halogen and the other of R$^2$ and R$^5$ is hydrogen, or both of R$^2$ and R$^5$ are halogen.

12. The compound of claim 8, wherein R$^1$ is —R$^7$ and R$^7$ is alkylaryl or alkylheteroaryl or R$^1$ is C(O)R$^7$, wherein R$^7$ is alkyl, haloalkyl, or substituted or unsubstituted aryl.

13. The compound of claim 8, wherein R$^6$ is not hydrogen.

14. The compound of claim 8, wherein R$^6$ is —NO$_2$ or —NHC(O)R$^8$.

15. The compound of claim 8, wherein the compound is selected from:

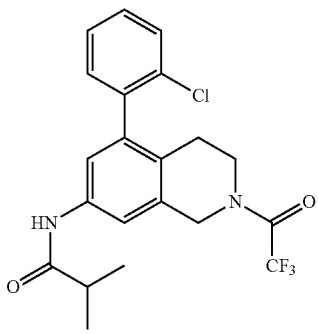

-continued

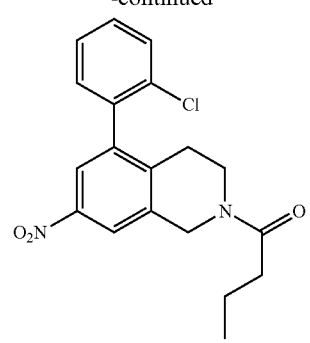

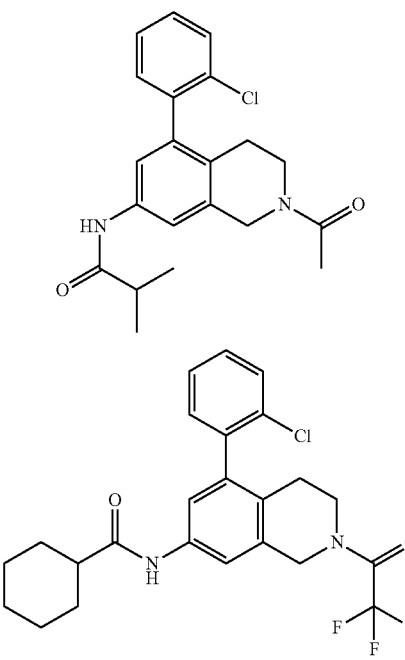

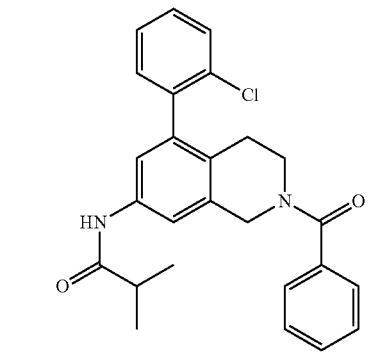

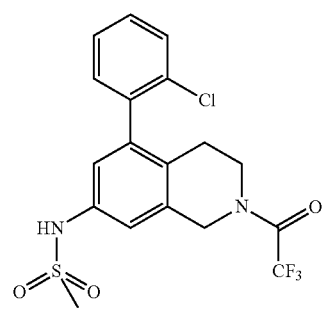

-continued

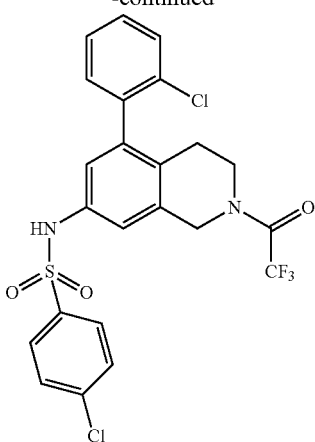

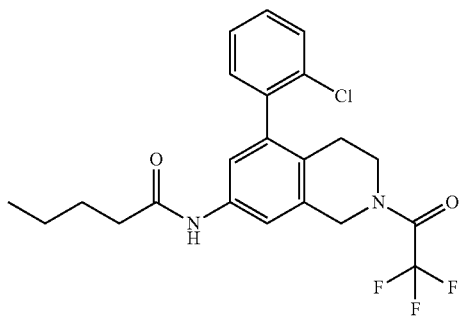

-continued

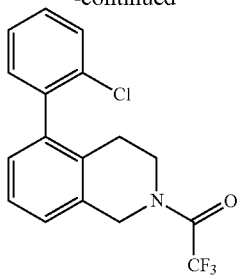

or a pharmaceutically acceptable salt thereof.

16. The compound of claim 4, wherein $R^{10}$ is —NHC(O)$R^{12}$, wherein $R^{12}$ is optionally substituted alkyl, cycloalkyl, or aryl.

17. The compound of claim 16, wherein $R^9$ is optionally substituted benzyl.

18. The compound of claim 11, wherein $R^1$ is —C(O)$R^7$, wherein $R^7$ is alkyl, haloalkyl, or substituted or unsubstituted aryl.

19. The compound of claim 18, wherein $R^6$ is —NHC(O)$R^8$, wherein $R^8$ is optionally substituted alkyl, cycloalkyl, or aryl.

20. A pharmaceutical composition comprising a compound as defined in claim 1 or a pharmaceutically acceptable salt thereof, optionally together with a pharmaceutically acceptable excipient and/or adjuvant and/or another therapeutically active agent.

21. A pharmaceutical composition comprising a compound as defined in claim 8 or a pharmaceutically acceptable salt thereof, optionally together with a pharmaceutically acceptable excipient and/or adjuvant and/or another therapeutically active agent.

* * * * *